United States Patent
Rogers et al.

[11] Patent Number: 6,166,015
[45] Date of Patent: Dec. 26, 2000

[54] PYRROLIDINE DERIVATIVES-CCR-3 RECEPTOR ANTAGONISTS

[75] Inventors: Daniel Harry Rogers; John Saunders; John Patrick Williams, all of San Diego, Calif.

[73] Assignee: Syntex (U.S.A.) Inc., Palo Alto, Calif.

[21] Appl. No.: 09/442,656

[22] Filed: Nov. 18, 1999

Related U.S. Application Data

[60] Provisional application No. 60/109,297, Nov. 20, 1998.

[51] Int. Cl.[7] .................. A61K 31/40; C07D 207/08; C07D 401/12; C07D 403/06
[52] U.S. Cl. ................. 514/243; 514/256; 514/274; 514/275; 514/422; 514/428; 544/184; 544/316; 544/332; 544/335; 548/526; 548/568
[58] Field of Search ................. 548/526, 568; 544/184, 316, 332, 335; 514/243, 256, 274, 275, 422, 428

[56] References Cited

U.S. PATENT DOCUMENTS

| | | | |
|---|---|---|---|
| 3,459,757 | 8/1969 | Wright, Jr. et al. | |
| 4,328,155 | 5/1982 | Masaru et al. | 548/567 |
| 4,328,344 | 5/1982 | Masaru et al. | 548/208 |
| 4,330,472 | 5/1982 | Ogata et al. | 548/567 |
| 4,350,635 | 9/1982 | Ogata et al. | 548/567 |
| 4,351,770 | 9/1982 | Ogata et al. | 548/567 |
| 4,431,663 | 2/1984 | Masaru et al. | 424/274 |
| 4,617,314 | 10/1986 | Tahara et al. | 514/422 |
| 4,895,841 | 1/1990 | Sugimoto et al. | 514/212 |
| 5,189,045 | 2/1993 | Peglion et al. | 514/319 |
| 5,208,243 | 5/1993 | Peglion et al. | 514/309 |
| 5,214,055 | 5/1993 | Peglion et al. | 514/320 |
| 5,254,569 | 10/1993 | Cheeseman et al. | 514/331 |
| 5,827,875 | 10/1998 | Dickson, Jr. et al. | 514/424 |

FOREIGN PATENT DOCUMENTS

| | | |
|---|---|---|
| 0 673 927 A1 | 9/1995 | European Pat. Off. |
| 0 903 349 A2 | 3/1999 | European Pat. Off. |
| 0 916 688 A1 | 5/1999 | European Pat. Off. |
| 6212757 | 7/1985 | Japan |
| 1117860 | 10/1987 | Japan |
| 2104572 | 10/1988 | Japan |
| 1-117860 | 5/1989 | Japan |
| WO 92/12128 | 7/1992 | WIPO |
| WO 92/22527 | 12/1992 | WIPO |
| WO 93/03725 | 3/1993 | WIPO |
| WO 96/34856 | 11/1996 | WIPO |
| 99/25686 | 5/1999 | WIPO |

OTHER PUBLICATIONS

Sudgen, *J. Medicinal Chemistry*, vol. 14:1, pp. 76–78 (1971) "Some Pyrrolidine Derivatives as Antispasmodics".
U.S. patent application SN 09/134,013, Filing date Aug. 14, 1998, *Cyclic Amine Derivatives CCR–3 Receptor Antagonists*, Gong, et al. (Assignee Syntex (U.S.A.) Inc); Docket No. R0029B–REG.

*Primary Examiner*—Fiona T. Powers
*Attorney, Agent, or Firm*—Rohan Peries

[57] ABSTRACT

This invention relates to certain 3-aminomethylpyrrolidine derivatives of Formula (I):

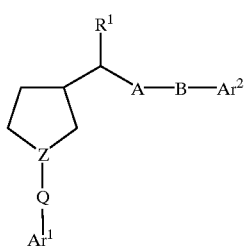

(I)

that are CCR-3 receptor antagonists, pharmaceutical compositions containing them, methods for their use and methods for preparing these compounds.

50 Claims, No Drawings

PYRROLIDINE DERIVATIVES-CCR-3 RECEPTOR ANTAGONISTS

CROSS REFERENCE TO RELATED APPLICATIONS

This application claims the benefit under 35 U.S.C. 119(e) of U.S. Provisional Application Ser. No. 60/109,297, filed Nov. 20, 1998, hereby incorporated by reference in its entirety.

FIELD OF THE INVENTION

This invention relates to certain pyrrolidine derivatives that are CCR-3 receptor antagonists, pharmaceutical compositions containing them, methods for their use and methods for preparing these compounds.

BACKGROUND INFORMATION

Tissue eosinophilia is a feature of a number of pathological conditions such as asthma, rhinitis, eczema and parasitic infections ((see Bousquet, J. et al., *N. Eng. J. Med.* 323: 1033–1039 (1990) and Kay, A. B. and Corrigan, C. J., *Br. Med. Bull.* 48:51–64 (1992)). In asthma, eosinophil accumulation and activation are associated with damage to bronchial epithelium and hyperresponsiveness to constrictor mediators. Chemokines such as RANTES, eotaxin and MCP-3 are known to activate eosinophils ((see Baggiolini, M. and Dahinden, C. A., *Immunol. Today.* 15:127–133 (1994), Rot, A. M. et al., *J. Exp. Med.* 176, 1489–1495 (1992) and Ponath, P. D. et al., *J. Clin. Invest.*, Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A. et al., *Biochem. Biophy. Res. Commun.* 197:1167 (1993) and Jose, P. J. et al., *Biochem. Biophy. Res. Commun.* 207, 788 (1994)). Specific eosinophil accumulation was observed at the site of administration of eotaxin whether by intradermal or intraperitoneal injection or aerosol inhalation ((see Griffith-Johnson, D. A. et al., *Biochem. Biophy. Res. Commun.* 197:1167 (1993); Jose, P. J. et al., *J. Exp. Med.* 179, 881–887 (1994); Rothenberg, M. E. et al., *J. Exp. Med.* 181, 1211 (1995) and Ponath, P. D., *J. Clin. Invest.*, Vol. 97, #3, 604–612 (1996)).

Glucocorticoids such as dexamethasone, methprednisolone and hydrocortisone have been used for treating many eosinophil-related disorders, including bronchial asthma ((R. P. Schleimer et al., *Am. Rev. Respir. Dis.*, 141, 559 (1990)). The glucocorticoids are believed to inhibit IL-5, IL-3 mediated eosinophil survival in these diseases. However, prolonged use of glucocorticoids can lead to side effects such as glaucoma, osteoporosis and growth retardation in the patients ((see Hanania, N. A. et al., *J. Allergy and Clin. Immunol.*, Vol. 96, 571–579 (1995) and Saha, M. T. et al., *Acta Paediatrica*, Vol. 86, #2, 138–142 (1997)). It is therefore desirable to have an alternative means of treating eosinophil related diseases without incurring these undesirable side effects.

Recently, the CCR-3 receptor was identified as a major chemokine receptor that eosinophils use for their response to eotaxin, RANTES and MCP-3. When transfected into a murine pre-β lymphoma line, CCR-3 bound eotaxin, RANTES and MCP-3 and conferred chemotactic responses on these cells to eotaxin, RANTES and MCP-3 ((see Ponath, P. D. et al., *J. Exp. Med.* 183, 2437–2448 (1996)). The CCR-3 receptor is expressed on the surface of eosinophils, T-cells (subtype Th-2), basophils and mast cells and is highly selective for eotaxin. Studies have shown that pretreatment of eosinophils with an anti-CCR-3 mAb completely inhibits eosinophil chemotaxis to eotaxin, RANTES and MCP-3 ((see Heath, H. et al., *J. Clin. Invest.*, Vol. 99, #2, 178–184 (1997)). Applicants' copending U.S. patent application Ser. No. 09/134,013, filed Aug. 14, 1998 discloses CCR-3 antagonists that inhibit eosinophilic recruitment by chemokine such as eotaxin.

Therefore, blocking the ability of the CCR-3 receptor to bind RANTES, MCP-3 and eotaxin and thereby preventing the recruitment of eosinophils should provide for the treatment of eosinophil-mediated inflammatory diseases.

The present invention concerns novel pyrrolidine derivatives which are capable of inhibiting the binding of eotaxin to the CCR-3 receptor and thereby provide a means of combating eosinophil induced diseases, such as asthma.

SUMMARY OF THE INVENTION

In a first aspect, this invention provides compounds selected from the group of compounds represented by Formula (I):

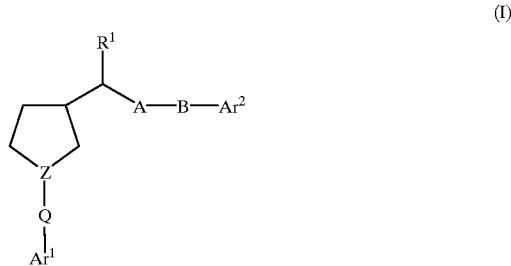

(I)

wherein:

Z is —N— or —(N$^+$R)—X$^-$ wherein R is alkyl, haloalkyl, aralkyl, hydroxyalkyl, carboxyalkyl, alkoxycarbonylalkyl, or cyanoalkyl, and X$^-$ is a pharmaceutically acceptable counterion;

Ar$^1$ and Ar$^2$ are, independently of each other, aryl or heteroaryl;

Q is a straight or branched alkylene chain of 1–3 carbon atoms;

R$^1$ is hydrogen or alkyl;

A is either:

(I) —N(R$^2$)C(O)— when:

B is:
(i) an alkylene chain of 1–4 carbon atoms inclusive wherein one of the carbon atoms may optionally be replaced by a group selected from —C(O)—, —N(R$^4$)—, —O—, —S(O)$_n$— (where n is 0, 1 or 2), —NR$^5$C(O)— and —N(R$^6$)SO$_2$—; or
(ii) an alkynylene chain;

wherein:
R$^2$ is hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; and R$^4$, R$^5$ and R$^6$ are, independently of each other, hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; or (II) a group selected from —N(R$^2$)C(S)—, —N(R$^2$)C(O)N(R$^3$)—, —N(R$^2$)C(S)N(R$^3$)—, —N(R$^2$)SO$_2$—, —N(R²)SO₂N(R³)—, —N(R²)C(O)O—, and —OC(O)N(R³)— when:

B is:
(i) a bond;
(ii) an alkylene chain of 1–4 carbon atoms inclusive wherein one of the carbon atoms may optionally be replaced by a group selected from —C(O)—, —N(R⁴)—, —O—, —S(O)$_n$— (where n is 0, 1 or 2), —NR⁵C(O)— and —N(R⁶)SO₂—;
(iii) an alkenylene chain; or
(iv) an alkynylene chain;

wherein:
R³ is hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; and R², R⁴, R⁵ and R⁶ are as defined above; and prodrugs, individual isomers, mixtures of isomers and pharmaceutically acceptable salts thereof.

In a second aspect, this invention provides pharmaceutical compositions containing a therapeutically effective amount of a compound of Formula (I) or its pharmaceutically acceptable salt and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or its pharmaceutically acceptable salt. The disease states include respiratory diseases such as asthma.

In a fourth aspect, this invention provides a process for preparing compounds of Formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenylene" means a linear divalent hydrocarbon radical of two to six carbon atoms or a branched divalent hydrocarbon radical of three to six carbon atoms, containing at least one double bond, e.g., ethenylene, 2,4-pentadienylene, and the like.

"Alkynylene" means a linear divalent hydrocarbon radical of two to six carbon atoms or a branched divalent hydrocarbon radical of three to six carbon atoms, containing at least one triple bond, e.g., ethynylene, propynylene, and the like.

"Acyl" means a radical —C(O)R where R is alkyl, haloalkyl, optionally substituted phenyl, optionally substituted phenylalkyl, optionally substituted heteroaralkyl or optionally substituted heteroaryl, e.g., acetyl, benzoyl, thenoyl, and the like.

"Halo" means fluoro, chloro, bromo or iodo, preferably fluoro and chloro.

"Haloalkyl" means alkyl substituted with one or more same or different halo atoms, e.g., —CH₂Cl, —CF₃, —CH₂CF₃, —CH₂CCl₃, and the like.

"Cycloalkyl" means a saturated monovalent cyclic hydrocarbon radical of three to six ring carbons, e.g., cyclopropyl, cyclohexyl, and the like.

"Monosubstituted-amino" means a radical —NHR where R is alkyl, heteroalkyl, haloalkyl, optionally substituted phenyl or optionally substituted heteroaryl, e.g., methylamino, (1-methylethyl)amino, phenylamino, and the like.

"Disubstituted-amino" means a radical —NRR' where R and R' are independently alkyl, heteroalkyl, haloalkyl, optionally substituted phenyl, or optionally substituted heteroaryl. Representative examples include, but are not limited to, dimethylamino, methylethylamino, di(1-methylethyl)amino, and the like.

"Aryl" means a monovalent monocyclic or bicyclic aromatic hydrocarbon radical of 6 to 10 ring atoms. The aryl ring may be optionally substituted independently with one or more substituents, preferably one, two or three substituents selected from alkyl, haloalkyl, alkylthio, heteroalkyl, alkoxy, cycloalkyl, cycloalkylalkyl, alkenyl, halo, cyano, nitro, optionally substituted phenyl, optionally substituted phenylalkyl, optionally substituted heteroaryl, optionally substituted heteroaralkyl, amino, monosubstituted amino, disubstituted amino, hydroxylamino, —OR [where R is hydrogen, haloalkyl, optionally substituted phenyl, optionally substituted phenylalkyl, optionally substituted heteroaryl or optionally substituted heteroaralkyl], —S(O)$_n$R [where n is an integer from 0 to 2 and R is alkyl, haloalkyl, optionally substituted phenyl, optionally substituted phenylalkyl, optionally substituted heteroaryl, optionally substituted heteroaralkyl, amino, mono- or disubstituted amino], —NRC(O)R' (where R is hydrogen or alkyl and R' is hydrogen, alkyl, heteroalkyl, haloalkyl, optionally substituted phenyl, or mono- or disubstituted amino), —NRSO₂R' (where R is hydrogen or alkyl and R' is alkyl, amino, mono- or disubstituted amino), —C(O)R (where R is hydrogen, alkyl, haloalkyl, optionally substituted phenyl or optionally substituted heteroaryl), —COOR (where R is hydrogen, alkyl, optionally substituted phenyl, optionally substituted phenylalkyl, optionally substituted heteroaryl or optionally substituted heteroaralkyl), -(alkylene)—COOR (where R is hydrogen, alkyl, optionally substituted phenyl, optionally substituted phenylalkyl, optionally substituted heteroaryl or optionally substituted heteroaralkyl), alkylenedioxy, oxy-C2-C3-alkylene, —CONR'R" or -(alkylene)—CONR'R" (where R' and R" are independently selected from hydrogen, alkyl, haloalkyl, optionally substituted phenyl, optionally substituted phenylalkyl, optionally substituted heteroaryl or optionally substituted heteroaralkyl). More specifically the term aryl includes, but is not limited to, phenyl, 1-naphthyl, 2-naphthyl, and derivatives thereof.

"Alkylenedioxy" is a divalent substituent of the formula —[—O—(CH₂)$_n$—O—]— (where n is 1 or 2) which is attached to two adjacent carbon atoms of phenyl, e.g., methylenedioxy-phenyl or ethylenedioxyphenyl.

"Oxy-C2-C3-alkylene" means a divalent substituent of the formula —[—O—(CH₂)$_n$—]— (where n is 2 or 3) which is attached to two adjacent carbons atoms of phenyl, e.g., oxyethylene or oxypropylene. An example of oxy-C2-C3-alkylenephenyl is 2,3-dihydrobenzofuranyl.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroaryl" means a monovalent monocyclic or bicyclic aromatic radical of 5 to 10 ring atoms containing one, two, or three ring heteroatoms selected from N, O, or S, the remaining ring atoms being C. The aromatic radical is optionally fused to a phenyl or an optionally substituted heteroaryl ring or it is optionally substituted independently with one or more substituents, preferably one or two substituents selected from alkyl, haloalkyl, heteroalkyl, alkoxy, halo, cyano, nitro, aryl, optionally substituted heteroaryl, amino, monosubstituted amino, disubstituted amino, hydroxyamino, —OR [where R is hydrogen, haloalkyl, or optionally substituted phenyl], —S(O)$_n$R [where n is an integer from 0 to 2 and R is alkyl, haloalkyl, optionally substituted phenyl, amino, mono or disubstituted amino], —C(O)R (where R is hydrogen, alkyl, haloalkyl or optionally substituted phenyl), —COOR (where R is hydrogen, alkyl or optionally substituted phenyl), -(alkylene)—COOR (where R is hydrogen, alkyl or optionally substituted phenyl), methylenedioxy, 1,2-ethylenedioxy, —CONR'R" or -(alkylene)—CONR'R" (where R' and R" are independently selected from hydrogen, alkyl, haloalkyl, or optionally substituted phenyl). More specifically the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, 9H-1,3,4,9-tetraazafluorene, and derivatives thereof.

"Optionally substituted heteroaryl" means a pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, 9H-1,3,4,9-tetraaza-fluorene ring which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heterocycle" or "Heterocyclyl" means a saturated or unsaturated cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclo ring may be optionally substituted independently with one, two or three substituents selected from alkyl, haloalkyl, cycloalkyl, cycloalkylalkyl, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or S(O)$_n$, where n is an integer from 0 to 2 and R is hydrogen, alkyl, haloalkyl, cycloalkyl, aralkyl, aryl, heteroaryl or heteroaralkyl), or —CONR'R" (where R' and R" are independently selected from hydrogen or alkyl). Representative examples include, but are not limited to, tetrahydropyranyl, piperidino, piperazino, pyrrolidino, and the like.

"Heteroalkyl" means an alkyl, cycloalkyl, or cycloalkylalkyl radical as defined above, carrying a substituent containing a heteroatom selected from N, O, S(O)$_n$ where n is an integer from 0 to 2. Representative substituents include —NR$^a$R$^b$, —OR$^a$ or —S(O)$_n$R$^c$, wherein n is an integer from 0 to 2, R$^a$ is hydrogen, alkyl, haloalkyl, cycloalkyl, cycloalkylalkyl, optionally substituted phenyl, optionally substituted phenylalkyl, optionally substituted heteroaryl, or —COR (where R is alkyl), R$^b$ is hydrogen, alkyl, —SO$_2$R (where R is alkyl or hydroxyalkyl), —SO$_2$NRR' (where R and R' are independently of each other hydrogen or alkyl), —CONR'R" (where R' and R" are independently selected from hydrogen or alkyl) and R$^c$ is hydrogen, alkyl, cycloalkyl, cycloalkylalkyl, optionally substituted phenyl, optionally substituted heteroaryl, amino, monosubstituted amino, or disubstituted amino. Representative examples include, but are not limited to 2-methoxyethyl, 2-hydroxyethyl, 2-aminoethyl, 2-dimethylaminoethyl, benzyloxymethyl, thiophen-2-ylthiomethyl, and the like.

"Hydroxyalkyl" means a linear monovalent hydrocarbon radical of two to six carbon atoms or a branched monovalent hydrocarbon radical of three or six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Cycloalkylalkyl" means a radical —R$^a$R$^b$ where R$^a$ is an alkylene group and R$^b$ is a cycloalkyl group as defined above e.g., cyclopropylmethyl, cyclohexylpropyl, 3-cyclohexyl-2-methylpropyl, and the like.

"Aralkyl" means a radical —R$^a$R$^b$ where R$^a$ is an alkylene group and R$^b$ is an aryl group as defined above e.g., benzyl, phenylethyl, 3-(3-chlorophenyl)-2-methylpentyl, and the like.

"Alkoxy" or "haloalkyloxy" means a radical —OR where R is an alkyl or haloalkyl, respectively as defined above e.g., methoxy, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Amino-protecting group" refers to those organic groups intended to protect nitrogen atoms against undesirable reactions during synthetic procedures e.g., benzyl, benzyloxycarbonyl (CBZ), t-butoxycarbonyl (BOC), trifluoroacetyl, and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^1$ substituent in a compound of Formula (I) is alkyl, then the carbon to which it is attached is an asymmetric center and the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable counterion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxylamino, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, sulfhydryl or amino group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations.

The pyrrolidine ring is numbered as follows:

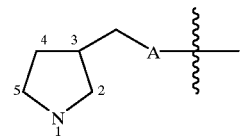

and the compounds of the invention are named as:

A compound of Formula (I) where Z is —N—, $Ar^1$ is 3,4-dichlorophenyl, Q is —CH$_2$—, $R^1$ is hydrogen, A is —NHCO—, B is —(CH$_2$)$_2$— and $Ar^2$ is 5-(4-methoxyphenyl)pyrimidin-2-yl, is named N-[1-(3,4-dichlorobenzyl)pyrrolidin-3-ylmethyl]-3-[5-(4-methoxyphenyl)-pyrimidin-2-yl]propionamide.

A compound of Formula (I) where Z is —N—, $Ar^1$ is 3,4-dichlorophenyl, Q is —CH$_2$—, $R^1$ is hydrogen, A is —NHCO—, B is —CH$_2$S— and $Ar^2$ is 5-(4-methoxyphenyl)pyrimidin-2-yl, is named N-[1-(3,4- dichlorobenzyl)pyrrolidin-3-ylmethyl]-2-[5-(4-methoxyphenyl)-pyrimidin-2-ylsulfanyl]acetamide.

A compound of Formula (I) where Z is —N—, $Ar^1$ is 3,4-dichlorophenyl, Q is —CH$_2$—, $R^1$ is hydrogen, A is —NHCO—, B is —CH$_2$O— and $Ar^2$ is 5-(4-methoxyphenyl)pyrimidin-2-yl, is named N-[1-(3,4-dichlorobenzyl)pyrrolidin-3-ylmethyl]-2-[5-(4-methoxyphenyl)-pyrimidin-2-yloxy]acetamide.

A compound of Formula (I) where Z is —N—, $Ar^1$ is 3,4-dichlorophenyl, Q is —CH$_2$—, $R^1$ is hydrogen, A is —NHCO—, B is —CH$_2$N— and $Ar^2$ is 5-(4-methoxyphenyl)pyrimidin-2-yl, is named N-[1-(3,4-dichlorobenzyl)pyrrolidin-3-ylmethyl]-2-[5-(4-methoxyphenyl)-pyrimidin-2-ylamino]acetamide.

A compound of Formula (I) where Z is —N—, $Ar^1$ is 3,4-methylenedioxyphenyl, Q is —CH$_2$—, $R^1$ is hydrogen, A is —NHCO—, B is —CH$_2$S— and $Ar^2$ is 5-(4-methoxyphenyl)-pyrimidin-2-yl, is named N-[1-(3,4-methylenedioxybenzyl)pyrrolidin-3-ylmethyl]-2-[5-(4-methoxyphenyl)pyrimidin-2-ylsulfanyl]acetamide.

A compound of Formula (I) where Z is —N—, $Ar^1$ is 3,4-dichlorophenyl, Q is —CH$_2$—, $R^1$ is hydrogen, A is —NHCO—, B is —CH$_2$— and $Ar^2$ is 4-methoxyphenyl, is named N-[1-(3,4-dichlorobenzyl)pyrrolidin-3-ylmethyl]-2-(4-methoxyphenyl)acetamide.

A compound of Formula (I) where Z is —N—, $Ar^1$ is 3,4-dichlorophenyl, Q is —CH$_2$—, $R^1$ is hydrogen, A is —NHCONH—, B is a bond and $Ar^2$ is 4-methoxyphenyl, is named 1-[1-(3,4-dichlorobenzyl)pyrrolidin-3-ylmethyl]-3-(4-methoxyphenyl)urea.

Representative compounds of this invention are as follows:
I. Representative compounds of Formula (I) where Z is —N—, $R^1$ is hydrogen and A is —NHCO—.

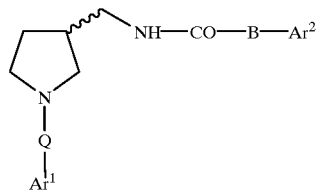

| CPD # | $Ar^1$ | Q | B | $Ar^2$ | Mass Spec. m/e |
|---|---|---|---|---|---|
| 1. | 2,3-dichlorophenyl | CH$_2$ | CH$_2$S | 5-(4-methoxyphenyl)pyrimidin-2-yl | 519 |
| 2. | 3,4-methylenedioxy-phenyl | CH$_2$ | CH$_2$S | 5-(4-methoxyphenyl)pyrimidin-2-yl.HCl | 493 |
| 3. | 2,3-dichlorophenyl | CH$_2$ | (CH$_2$)$_2$ | 5-(4-methoxyphenyl)pyrimidin-2-yl | 500 |
| 4. | 3,4-dichlorophenyl | CH$_2$ | CH$_2$S | 5-(4-methoxyphenyl)pyrimidin-2-yl | 519 |
| 5. | 2,3-dichlorophenyl | CH$_2$ | CH$_2$S | 5-(4-methoxyphenyl)pyrimidin-2-yl.HCl | |
| 6. | 2,3-dichlorophenyl | CH$_2$ | (CH$_2$)$_2$ | 5-(4-dimethylaminophenyl)pyrimidin-2-yl | 514 |
| 7. | 2,3-dichlorophenyl | CH$_2$ | (CH$_2$)$_2$ | 5-(4-methoxyphenyl)pyrimidin-2-yl | 499 |
| 8. | 3,4-methylenedioxy-phenyl | CH$_2$ | CH$_2$S | 5-(4-methoxyphenyl)pyrimidin-2-yl | 494 |
| 9. | 2,3-dichlorophenyl | CH$_2$ | CH$_2$O | 5-(4-methoxyphenyl)pyrimidin-2-yl | 502 |
| 10. | 3,4-methylenedioxy-phenyl | CH$_2$ | (CH$_2$)$_2$ | 5-(4-methoxyphenyl)pyrimidin-2-yl | 476 |
| 11. | 3-chlorophenyl | CH$_2$ | (CH$_2$)$_2$ | 5-(4-methoxyphenyl)pyrimidin-2-yl | 466 |
| 12. | 3,4-dichlorophenyl | CH$_2$ | CH$_2$S | 9H-1,3,4,9-tetraaza-fluoren-2-yl.TFA | 501 |
| 13. | 3,4-methylenedioxy-phenyl | CH$_2$ | CH$_2$S | 5-phenylpyrimidin-2-yl | 464 |
| 14. | 3,4-dichlorophenyl | CH$_2$ | (CH$_2$)$_2$ | 5-(4-methoxyphenyl)pyrimidin-2-yl | 500 |
| 15. | 3,4-dichlorophenyl | CH$_2$ | CH$_2$NHSO$_2$ | phenyl.TFA | |
| 16. | 2,3-dichlorophenyl | CH$_2$ | CH$_2$O | 5-(4-methylthiophenyl)pyrimidin-2-yl | 518 |
| 17. | 3-chlorophenyl | CH$_2$ | CH$_2$S | 5-(4-methoxyphenyl)pyrimidin-2-yl | 484 |
| 18. | 3,4-dichlorophenyl | CH$_2$ | CH$_2$S | 5-(4-methoxyphenyl)pyrimidin-2-yl | 519 |
| 19. | 2,3-dichlorophenyl | CH$_2$ | CH$_2$O | 5-benzofuran-2-ylpyrimidin-2-yl | 512 |
| 20. | 2,3-dichlorophenyl | CH$_2$ | CH$_2$S | 5-phenylpyrimidin-2-yl | 489 |
| 21. | 3,4-methylenedioxy-phenyl | CH$_2$ | CH$_2$O | 5-(4-methoxyphenyl)pyrimidin-2-yl | 477 |
| 22. | 2,3-methylenedioxy-phenyl | CH$_2$ | CH$_2$S | 5-(4-methoxyphenyl)pyrimidin-2-yl | 494 |
| 23. | 3,4-dichlorophenyl | CH$_2$ | CH$_2$O | 5-(4-methoxyphenyl)pyrimidin-2-yl | 502 |
| 24. | 3-chlorophenyl | CH$_2$ | (CH$_2$)$_2$ | 5-(4-dimethylaminophenyl)pyrimidin-2-yl | 479 |
| 25. | 2,3-dichlorophenyl | CH$_2$ | CH$_2$S | 5-(4-methylphenyl)pyrimidin-2-yl | 503 |
| 26. | 3,4-dichlorophenyl | CH$_2$ | CH$_2$S | 5-phenylpyrimidin-2-yl | |
| 27. | 3,4-dichlorophenyl | CH$_2$ | (CH$_2$)$_2$ | 5-(4-dimethylaminophenyl)pyrimidin-2-yl | 514 |
| 28. | 2,3-dichlorophenyl | CH$_2$ | CH$_2$O | 5-(4-methylphenyl)pyrimidin-2-yl | 486 |
| 29. | 3,4-methylenedioxy-phenyl | CH$_2$ | CH$_2$S | 5-phenylpyrimidin-2-yl | 464 |
| 30. | 2,3-dichlorophenyl | CH$_2$ | CH$_2$O | 5-(4-fluorophenyl)pyrimidin-2-yl | 490 |
| 31. | 3-chlorophenyl | CH$_2$ | CH$_2$S | 5-phenylpyrimidin-2-yl | 454 |
| 32. | 2,3-dichlorophenyl | CH$_2$ | CH$_2$S | 5-phenylpyrimidin-2-yl | 489 |
| 33. | 3,4-methylenedioxy-phenyl | CH$_2$ | CH$_2$O | 5-(4-methoxyphenyl)pyrimidin-2-yl | 477 |
| 34. | 3,4-methylenedioxy- | CH$_2$ | CH$_2$S | 5-(4-chlorophenyl)pyrimidin-2-yl | 498 |

-continued

| | | | | | |
|---|---|---|---|---|---|
| 35. | naphth-2-yl | $CH_2$ | $(CH_2)_2$ | 5-(4-methoxyphenyl)pyrimidin-2-yl | 482 |
| 36. | 2,3-dichlorophenyl | $CH_2$ | $CH_2O$ | 5-(4-vinylphenyl)pyrimidin-2-yl | 498 |
| 37. | 2,3-dichlorophenyl | $CH_2$ | $CH_2S$ | 5-(4-chlorophenyl)pyrimidin-2-yl | 523 |
| 38. | 3,4-methylenedioxyphenyl | $CH_2$ | $CH_2S$ | 5-(4-methylphenyl)pyrimidin-2-yl | 478 |
| 39. | 2,3-dichlorophenyl | $CH_2$ | $(CH_2)_2$ | 5-(4-methylphenyl)pyrimidin-2-yl | 484 |
| 40. | 2,3-dichlorophenyl | $CH_2$ | $CH_2N$ | 5-(4-methoxyphenyl)pyrimidin-2-yl | |
| 41. | 2,3-dichlorophenyl | $CH_2$ | $(CH_2)_2$ | 1-(4-aminosulfonylphenyl)pyrazol-4-yl | 537 |
| 42. | 3,4-dichlorophenyl | $CH_2$ | $CH_2S$ | pyrimidin-2-yl.HCl | |
| 43. | 3,4-dichlorophenyl | $CH_2$ | $CH_2S$ | pyridin-4-yl.TFA | 410 |
| 44. | 3,4-dichlorophenyl | $CH_2$ | $CH_2S$ | 4-amino-5-(3-chlorophenyl)pyrimidin-2-yl | 536 |
| 45. | 3,4-dichlorophenyl | $CH_2$ | $CH_2S$ | quinoxalin-2-yl | 461 |
| 46. | 3,4-methylenedioxyphenyl | $CH_2$ | $CH_2O$ | 5-(4-methythiophenyl)pyrimidin-2-yl | 493 |
| 47. | 3,4-dichlorophenyl | $CH_2$ | $CH_2S$ | naphth-2-yl.TFA | 459 |
| 48. | 3,4-dichlorophenyl | $CH_2$ | $CH_2$ | 1-phenyl-5-methylpyrazol-4-yl.TFA | 457 |
| 49. | 3,4-methylenedioxyphenyl | $CH_2$ | $(CH_2)_2$ | 5-(2-methyphenyl)pyrimidin-2-yl | 460 |
| 50. | naphth-2-yl | $CH_2$ | $(CH_2)_2$ | 5-(2-methyphenyl)pyrimidin-2-yl | 466 |
| 51. | 2,3-dichlorophenyl | $CH_2$ | $(CH_2)_2$ | 1-(4-methylphenyl)pyrazol-4-yl | 537 |
| 52. | 3,4-dichlorophenyl | $CH_2$ | $(CH_2)_2$ | 2-bromo-4,5-dimethoxyphenyl.TFA | 383 |
| 53. | 3,4-dichlorophenyl | $CH_2$ | $CH_2$ | thiophen-3-yl.TFA | |
| 54. | 3,4-methylenedioxyphenyl | $CH_2$ | $CH_2O$ | 5-(benzofuran-2-yl)pyrimidin-2-yl | 487 |
| 55. | 3,4-dichlorophenyl | $CH_2$ | $CH_2S$ | 4-methylpyrimidin-2-yl.TFA | 425 |
| 56. | 3,4-dichlorophenyl | $CH_2$ | $CH_2S$ | 4-aminophenyl.TFA | |
| 57. | 2,3-dichlorophenyl | $CH_2$ | $(CH_2)_2$ | 1-[4-(2-propylphenyl)]pyrazol-4-yl | 461 |
| 58. | 6-chloro-3,4-methylenedioxyphenyl | $CH_2$ | $CH_2S$ | 5-(4-methoxyphenyl)pyrimidin-2-yl | 528 |
| 59. | 3,4-dichlorophenyl | $CH_2$ | $CH_2O$ | 4-benzyloxyphenyl.TFA | 499 |
| 60. | 3,4-dichlorophenyl | $CH_2$ | $(CH_2)_3CO$ | thiophen-2-yl.TFA | 439 |
| 61. | 3,4-dichlorophenyl | $CH_2$ | $(CH_2)_2$ | 1-benzylpyrazol-4-yl | 452 |
| 62. | 3,4-dichlorophenyl | $CH_2$ | $CH_2O$ | 4-acetylphenyl.TFA | 435 |
| 63. | 3,4-dichlorophenyl | $CH_2$ | $(CH_2)_2$ | 3-hydroxyphenyl.TFA | 407 |
| 64. | 3,4-dichlorophenyl | $CH_2$ | $CH_2$ | 3-(thiophen-2-yl)pyrazol-1-yl | 449 |
| 65. | 3,4-dichlorophenyl | $CH_2$ | $(CH_2)3$ | 3,4-dimethoxyphenyl.TFA | 465 |
| 66. | 3,4-dichlorophenyl | $CH_2$ | $CH_2$ | 5,6-dimethylbenzimidazol-1-yl.TFA | 445 |
| 67. | 3,4-dichlorophenyl | $CH_2$ | $CH_2S$ | 5-trifluoromethylpyridin-2-yl | |
| 68. | 3,4-dichlorophenyl | $CH_2$ | $(CH_2)_3O$ | 4-chloro-3-methylphenyl.TFA | |
| 69. | 3,4-dichlorophenyl | $CH_2$ | $(CH_2)_2CO$ | naphth-1-yl.TFA | 469 |
| 70. | 4-fluoro-3-methoxyphenyl | $CH_2$ | $CH_2O$ | 5-(4-methoxyphenyl)pyrimidin-2-yl | 481 |
| 71. | 2,3-dichlorophenyl | $CH_2$ | $(CH_2)_2$ | 1-(2,6-dimethylpyrimidin-4-yl)pyrazol-4-yl | 488 |
| 72. | 3,4-dichlorophenyl | $CH_2$ | $(CH_2)_3O$ | 2,4-dichlorophenyl.TFA | 490 |
| 73. | 3,4-dichlorophenyl | $CH_2$ | $CH_2S$ | 4,6-dimethoxy-5-phenylpyrimidin-2-yl | 519 |
| 74. | 3,4-dichlorophenyl | $(CH_2)3$ | $CH_2S$ | 5-(4-methoxyphenyl)pyrimidin-2-yl | 546 |
| 75. | 3,4-dichlorophenyl | $CH_2$ | $CH_2$ | indol-1-yl.TFA | 416 |
| 76. | 3,4-dichlorophenyl | $CH_2$ | $CH_2S$ | 2-(pyridin-2-yl)-4-trifluoromethyl-pyrimidin-6-yl.TFA | 556 |
| 77. | 3,4-dichlorophenyl | $CH_2$ | $CH_2N(CH_3)CO$ | phenyl | |
| 78. | 3,4-dichlorophenyl | $CH_2$ | $(CH_2)_2CO$ | 4-methoxynaphth-1-yl.TFA | |
| 79. | 3,4-dichlorophenyl | $CH_2$ | $CH_2O$ | 4-hydroxymethylphenyl.TFA | 423 |
| 80. | 3,4-ethylenedioxyphenyl | $CH_2$ | $CH_2S$ | 5-(4-methylphenyl)pyrimidin-2-yl | 492 |
| 81. | 3,4-dichlorophenyl | $CH_2$ | $CH_2SO_2$ | 4-methylphenyl.TFA | 455 |
| 82. | 3,4-dichlorophenyl | $CH_2$ | $(CH_2)_2$ | 1-(quinoxalin-2-yl)pyrazol-4-yl | 510 |
| 83. | 3,4-dichlorophenyl | $CH_2$ | $CH_2S$ | 5-(4-chlorophenyl)pyrimidin-4-yl | |
| 84. | 3,4-dichlorophenyl | $CH_2$ | $(CH_2)_2CO$ | 4-methylsulfonylphenyl.TFA | 497 |
| 85. | 3,4-dichlorophenyl | $CH_2$ | $(CH_2)_2CO$ | 3,6-dimethoxynaphth-2-yl.TFA | 529 |
| 86. | 3,4-dichlorophenyl | $CH_2$ | $CH(CH_3)_O$ | 1-acetylnaphth-2-yl.TFA | 499 |
| 87. | 2,3-dichlorophenyl | $CH_2$ | $CH_2$ | 3-(2,5-difluoro-4-chlorophenylcarbonylamino)phenyl | |
| 88. | 2,3-dichlorophenyl | $CH_2$ | $CH_2$ | 3-(2,3,4,5-tetrafluorophenylcarbonylamino)phenyl | |
| 89. | 2,3-dichlorophenyl | $CH_2$ | $CH_2$ | 3-(acetylamino)phenyl | |
| 90. | 2,3-dichlorophenyl | $CH_2$ | $CH_2$ | 3-fluoro-4-hydroxyphenyl | 411 |
| 91. | 3,4-methylenedioxyphenyl | $CH_2$ | $CH_2$ | 3-(2,4-dimethoxyphenylcarbonylamino)phenyl | |
| 92. | 3,4-dichlorophenyl | $CH_2$ | $CH_2$ | 4-methylsulfonylphenyl | |
| 93. | 3,4-dichlorophenyl | $CH_2$ | *$CH(CH_3)$ <br> * = (R) stereochem. | 6-methoxynaphth-2-yl | 471 |
| 94. | 3,4-dichlorophenyl | $CH_2$ | $CH_2$ | 5-benzoylthiophen-2-yl.TFA | 487 |
| 95. | 3,4-dichlorophenyl | $CH_2$ | $CH_2$ | 3-fluoro-4-hydroxyphenyl | 411 |
| 96. | 3,4-methylenedioxyphenyl | $CH_2$ | $CH_2S$ | 9 H-1,3,4,9-tetraazafluoren-2-yl.TFA | 477 |
| 97. | 2,3-dichlorophenyl | $CH_2$ | $CH_2O$ | 5-(3,4-methylenedioxyphenyl)pyrimidin-2-yl | 531 |
| 98. | 3,4-dichlorophenyl | $CH_2$ | $(CH_2)_2$ | 5-(3,4-methylenedioxyphenyl)pyrimidin-2-yl | 529 |

-continued

| | | | | | |
|---|---|---|---|---|---|
| 99. | 2,3-dichlorophenyl | CH$_2$ | (CH$_2$)$_2$ | 5-(3,4-methylenedioxyphenyl)pyrimidin-2-yl | 529 |
| 100. | 2,3-dichloro-thiophen-5-yl | CH$_2$ | CH$_2$S | 5-(3,4-methylenedioxyphenyl)pyrimidin-2-yl | 553 |
| 101. | 2,3-dichlorophenyl | CH(CH$_3$) | CH$_2$S | 5-(3,4-methylenedioxy)pyrimidin-2-yl | 561 |
| 102. | 3,4-dichlorophenyl | CH$_2$ | CH$_2$S | 5-(3,4-dimethoxyphenyl)pyrimidin-2-yl | 547 |

II. Representative compounds of Formula (I) where Z is —N—, R$^1$ is hydrogen and A is —NHCONH—.

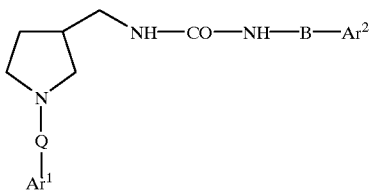

| CPD # | Ar$^1$ | Q | B | Ar$^2$ | Mass Spec. m/e |
|---|---|---|---|---|---|
| 103. | 3,4-methylenedioxyphenyl | CH$_2$ | CH$_2$ | 3-methylphenyl.TFA | 382 |
| 104. | 3,4-methylenedioxyphenyl | CH$_2$ | bond | 3-methylphenyl.TFA | 368 |
| 105. | 3,4-dichlorophenyl | CH$_2$ | CH$_2$ | 4-pyridyl | |
| 106. | 2,3-dichlorophenyl | CH$_2$ | CH$_2$ | 4-methoxyphenyl | 423 |
| 107. | 3-biphenyl | CH$_2$ | bond | 3-methylphenyl.TFA | 400 |
| 108. | 3,4-dichlorophenyl | CH$_2$ | CH$_2$ | 2-pyridyl | |
| 109. | 3,4-dichlorophenyl | CH$_2$ | CH$_2$ | 3-fluoro-5-trifluoromethylphenyl | |
| 110. | 3,4-dichlorophenyl | CH$_2$ | bond | 2-methoxyphenyl | 408 |
| 111. | 3,4-dichlorophenyl | CH$_2$ | (CH$_2$)$_2$ | phenyl.TFA | 406 |
| 112. | 3,4-dichlorophenyl | (CH$_2$)$_2$ | bond | 3-methoxyphenyl.TFA | 422 |
| 113. | naphth-2-yl | CH$_2$ | CH$_2$ | 4-methoxyphenyl | 405 |
| 114. | 3,4-dichlorophenyl | CH$_2$ | bond | 3-methoxycarbonylphenyl | 436 |
| 115. | 3,4-dichlorophenyl | (CH$_2$)$_3$ | bond | 3-chlorophenyl.TFA | 422 |
| 116. | 3,4-dichlorophenyl | (CH$_2$)$_2$ | (CH$_2$)$_2$ | phenyl.TFA | 420 |
| 117. | 3,4-dichlorophenyl | CH$_2$ | bond | 4-phenoxyphenyl | 484 |
| 118 | 5-bromothiophen-2-yl | CH$_2$ | bond | 3-methoxyphenyl | 440 |
| 119 | 3,4-dichlorophenyl | CH$_2$ | —CO— | phenyl.TFA | |

III. Representative compounds of Formula (I) where Z is —N—, R$^1$ is hydrogen and A is —NHC(S)NH—.

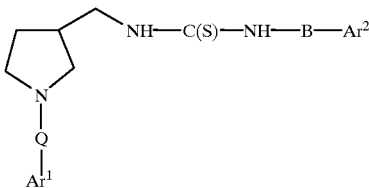

| CPD # | Ar$^1$ | Q | B | Ar$^2$ | Mass Spec. m/e |
|---|---|---|---|---|---|
| 120. | 3,4-dichlorophenyl | CH$_2$ | bond | 4-dimethylaminpophenyl | |
| 121. | 3-phenyl | (CH$_2$)$_3$ | bond | 4-dimethylaminophenyl | 400 |

IV. Representative compounds of Formula (I) where Z is —N—, R$^1$ is hydrogen and A is —NHSO$_2$—.

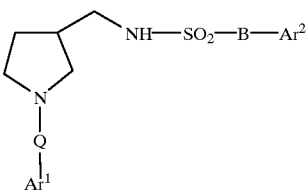

| CPD # | Ar$^1$ | Q | B | Ar$^2$ | Mass Spec. m/e |
|---|---|---|---|---|---|
| 122. | 3-(3,4-dichlorophenoxy)phenyl | CH$_2$ | CH$_2$ | phenyl | 506 |
| 123. | 8-carboxynaphth-1-yl | CH$_2$ | CH$_2$ | phenyl | 482 |

V. Representative compounds of Formula (I) where Z is —(NR$^5$)— X$^-$, R$^1$ is hydrogen and A is —NHCONH—.

-continued

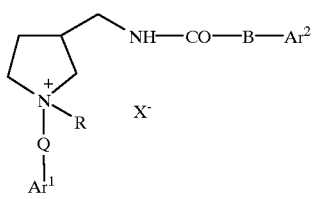

| CPD # | Ar¹ | Q | B | R | X⁻ | Ar² |
|---|---|---|---|---|---|---|
| 124. | 3,4-dichlorophenyl | $CH_2$ | $CH_2S$ | $CH_3$ | iodide | 5-(4-methoxyphenyl)pyrimidin-2-yl |

PREFERRED EMBODIMENTS

While the broadest definition of this invention is set forth in the Summary of the Invention, certain compounds of Formula (I) are preferred.

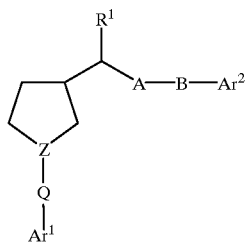

(I)

(I) One preferred group of compounds is that wherein:
$R^1$ is hydrogen; and
A is —NHCO—.

Within this group, a more preferred group of compounds is that wherein:
(a) Z is —N—; and
$Ar^1$ is a naphthyl or a substituted phenyl ring.

Within these preferred and more preferred groups, an even more preferred group of compounds is that wherein:
The stereochemistry at the C-3 carbon of the pyrrolidine ring is (S);
Q is a straight or branched alkylene chain of 1 to 3 carbon atoms, preferably —$CH_2$—, —$CH(CH_3)$—, —$C(CH_3)_2$—;
B are —$CH_2$—;
$Ar^1$ is a phenyl ring substituted with one, two or three substituents selected from alkyl, cyano, nitro, halo, alkylenedioxy, oxy-C2-C3-alkylene, alkoxy or phenoxy, preferably a phenyl ring substituted with one or two substituents selected from methyl, chloro, fluoro, bromo, or methylenedioxy; and
$Ar^2$ is an aryl ring, preferably a phenyl ring which is optionally substituted with one, two, or three substituents selected from alkoxy, alkylthio, halo, amino, —NHC(O)R' (where R' is alkyl or optionally substituted phenyl), hydroxy, or —$SO_2Me$, preferably a phenyl ring optionally substituted with one, two, or three substituents selected from methyl, methylthio, hydroxy, methoxy, acetyl, chloro, fluoro, bromo, or —NHC(O)R' (where R' is methyl or a phenyl ring optionally substituted with one, two or three substituents selected from methyl, methoxy, fluoro or chloro).

Within these preferred and more preferred groups, particularly preferred group of compounds is that wherein:
$Ar^1$ is 3-chlorophenyl, 4-chlorophenyl, 4-fluoro-3-methoxyphenyl, 2,4-difluorophenyl, 3,4-difluorophenyl, 3-chloro-4-fluorophenyl, 4-chloro-3-fluorophenyl, 3,4-ethylenedioxyphenyl, 2-naphthyl, 2,3-dichlorophenyl, 3,4-dichlorophenyl, 3,4-methylenedioxyphenyl, most preferably 2,3-dichlorophenyl, 3,4-dichlorophenyl or 3,4-methylenedioxyphenyl; and
$Ar^2$ is phenyl, 3-(2,5-difluoro-4-chlorophenylcarbonylamino)phenyl, 4-(2,3,4,5-tetrafluorophenylcarbonylamino)phenyl, 3-(2,4-dimethoxyphenylcarbonylamino)phenyl, 3-(phenylcarbonylamino)phenyl, 3-acetylaminophenyl, 3-fluoro-4-hydroxyphenyl, 3-fluorophenyl, 3-methoxyphenyl or 4-hydroxy-3-methoxyphenyl, most preferably 3-(2,5-difluoro-4-chlorophenylcarbonylamino)phenyl, 3-acetylaminophenyl, 3-(2,4-dimethoxyphenylcarbonylamino)phenyl or 3-(phenylcarbonylamino)phenyl.

(b) A second more preferred group of compounds in group (I) is that wherein:
Z is —N—; and
B is alkylene chain, preferably —$(CH_2)_2$—.

Within this more preferred group, an even more preferred group of compounds is that wherein:
The stereochemistry at the C-3 carbon of the pyrrolidine ring is (S);
Q is a straight or branched alkylene chain of 1 to 3 carbon atoms, preferably —$CH_2$—, —$CH(CH_3)$—, —$C(CH_3)_2$—; and
$Ar^1$ is naphthyl or a substituted phenyl ring.

Within these more preferred and even more preferred groups, a particularly preferred group of compounds is that wherein:
$Ar^1$ is a phenyl ring substituted with one, two or three substituents selected from alkyl, cyano, nitro, halo, alkylenedioxy, oxy-C2-C3-alkylene, alkoxy or phenoxy, preferably one or two substituents selected from methyl, chloro, fluoro, bromo, methylenedioxy; more preferably 3-chlorophenyl, 4-chlorophenyl, 4-fluoro-3-methoxyphenyl, 2,4-difluorophenyl, 3,4-difluorophenyl, 3-chloro-4-fluorophenyl, 4-chloro-3-fluorophenyl, 3,4-ethylenedioxyphenyl, 2-naphthyl, 2,3-dichlorophenyl, 3,4-dichlorophenyl, 3,4-methylenedioxyphenyl, most preferably 2,3-dichlorophenyl, 3,4-dichlorophenyl or 3,4-methylenedioxyphenyl.

Within the above preferred, more preferred group and particularly preferred groups, an even more preferred group of compounds is that wherein:

(i) $Ar^2$ is a pyrimidin-2-yl ring optionally substituted with alkyl or a phenyl ring optionally substituted with one, two, or three substituents selected from alkyl, alkoxy, alkylthio, halo, alkenyl, amino, monosubstituted amino, disubstituted amino, or benzofuran-2-yl, preferably a pyrimidin-2-yl ring optionally substituted with a phenyl ring optionally substituted with one, two, or three substituents selected from methyl, methoxy, methylthio, chloro, fluoro, vinyl, dimethylamino, most preferably pyrimidin-2-yl, 5-(benzofuran-2-yl)pyrimidin-2-yl, 5-phenylpyrimidin-2-yl, 5-(4-methoxyphenyl)-pyrimidin-2-yl, 5-(3,4-dimethoxyphenyl)pyrimidin-2-yl, 5-(4-dimethylamino-phenyl)pyrimidin-2-yl, 5-(4-methylphenyl)pyrimidin-2-yl, 5-(4-methylthiophenyl)pyrimidin-2-yl, 5-(4-vinylphenyl)pyrimidin-2-yl, or 5-(4-fluorophenyl)pyrimidin-2-yl.

Another particularly preferred group of compounds is that wherein:

(ii) $Ar^2$ is a pyrazolyl ring optionally substituted with one or two substituents selected from alkyl or phenyl which is optionally substituted with a group selected from alkyl, halo or —$SO_2R$ (where R is alkyl, alkoxy, amino, mono- or disubstituted amino), preferably pyrazol-4-yl optionally substituted with one or two substituents selected from methyl or phenyl which is optionally substituted with a group selected from methyl, 2-propyl, fluoro, chloro, methoxy or —$SO_2NH_2$, more preferably 1-(4-methylphenyl)pyrazol-4-yl, 1-[4-(2-propyl)phenyl]pyrazol-4-yl, 1-(4-aminosulfonylphenyl)pyrazol-4-yl or 1-(4-fluorophenyl)pyrazol-4-yl.

(iii) A third particularly preferred group of compounds is that wherein:

$Ar^2$ is:
pyridyl, preferably 4-pyridyl;
quinoxaline, preferably quinoxalin-2-yl; or
9H-1,3,4,9-tetraazafluorene, preferably 9H-1,3,4,9-tetraaza-fluor-2-ene.

(c) A third more preferred group of compounds in group (I) is that wherein:
Z is —N—; and
B is —$CH_2S$—.

Within these preferred and more preferred groups, an even more preferred group of compounds is that wherein:
The stereochemistry at the C-3 carbon of the pyrrolidine ring is (S);
Q is a straight or branched alkylene chain of 1 to 3 carbon atoms, preferably —$CH_2$—, —$CH(CH_3)$—, —$C(CH_3)_2$—; and
$Ar^1$ is naphthyl or a substituted phenyl ring.

Within these preferred and more preferred groups, particularly preferred group of compounds is that wherein:
$Ar^1$ is a phenyl ring which is optionally substituted with one, two or three substituents selected from alkyl, cyano, nitro, halo, alkylenedioxy, oxy-C2-C3-alkylene, alkoxy or phenoxy, preferably one or two substituents selected from methyl, chloro, fluoro, bromo, methylenedioxy; more preferably 3-chlorophenyl, 4-chlorophenyl, 4-fluoro-3-methoxyphenyl, 2,4-difluorophenyl, 3,4-difluorophenyl, 3-chloro-4-fluorophenyl, 4-chloro-3-fluorophenyl, 3,4-ethylenedioxyphenyl, 2-naphthyl, 2,3-dichlorophenyl, 3,4-dichlorophenyl, 3,4-methylenedioxyphenyl, most preferably 2,3-dichlorophenyl, 3,4-dichlorophenyl or 3,4-methylenedioxyphenyl.

Within the above preferred, more preferred group and particularly preferred groups, an even more preferred group of compounds is that wherein:

(i) $Ar^2$ is pyrimidin-2-yl ring optionally substituted with alkyl or a phenyl ring which is optionally substituted with one, two, or three substituents selected from alkyl, alkoxy, alkylthio, halo, alkenyl, amino, monosubstituted amino, disubstituted amino or benzofuran-2-yl, preferably a pyrimidin-2-yl ring optionally substituted with a phenyl ring which is optionally substituted with one, two, or three substituents selected from methyl, methoxy, methylthio, chloro, fluoro, vinyl, dimethylamino, most preferably pyrimidin-2-yl, 5-(benzofuran-2-yl)pyrimidin-2-yl, 5-phenylpyrimidin-2-yl, 5-(4-methoxyphenyl)-pyrimidin-2-yl, 5-(3,4-dimethoxyphenyl)-pyrimidin-2-yl, 5-(4-dimethylaminophenyl)-pyrimidin-2-yl, 5-(4-methylphenyl)pyrimidin-2-yl, 5-(4-methylthiophenyl)pyrimidin-2-yl, 5-(4-vinylphenyl)pyrimidin-2-yl, or 5-(4-fluorophenyl)pyrimidin-2-yl.

(ii) Another particularly preferred group of compounds is that wherein:

$Ar^2$ is a pyrazolyl ring optionally substituted with one or two substituents selected from alkyl or phenyl which is optionally substituted with a group selected from alkyl, halo, or —$SO_2R$ (where R is alkyl, alkoxy, amino, mono- or disubstituted amino), preferably pyrazol-4-yl optionally substituted with one or two substituents selected from methyl or phenyl which is optionally substituted with a group selected from methyl, 2-propyl, fluoro, chloro, methoxy, or —$SO_2NH_2$, more preferably 1-(4-methylphenyl)-pyrazol-4-yl, 1-(4-methoxyphenyl)pyrazol-4-yl, 1-[4-(2-propyl)phenyl]pyrazol-4-yl, 1-(4-aminosulfonylphenyl)pyrazol-4-yl or 1-(4-fluorophenyl)pyrazol-4-yl.

(iii) A third particularly preferred group of compounds is that wherein:

$Ar^2$ is:
pyridyl, preferably 4-pyridyl;
quinoxaline, preferably quinoxalin-2-yl; or
9H-1,3,4,9-tetraazafluorene, preferably 9H-1,3,4,9-tetraaza-fluor-2-ene.

(d) A third more preferred group of compounds in group (I) is that wherein:
Z is —N—; and
B is —$CH_2O$—.

Within these preferred and more preferred groups, an even more preferred group of compounds is that wherein:
The stereochemistry at the C-3 carbon of the pyrrolidine ring is (S);
Q is a straight or branched alkylene chain of 1 to 3 carbon atoms, preferably —$CH_2$—, —$CH(CH_3)$—, —$C(CH_3)_2$—; and
$Ar^1$ is naphthyl or a substituted phenyl ring.

Within these preferred and more preferred groups, particularly preferred group of compounds is that wherein:
$Ar^1$ is a phenyl ring which is optionally substituted with one, two, or three substituents selected from alkyl, cyano, nitro, halo, alkylenedioxy, oxy-C2-C3-alkylene, alkoxy or phenoxy, preferably one or two substituents selected from methyl, chloro, fluoro, bromo, methylenedioxy; more preferably 3-chlorophenyl, 4-chlorophenyl, 4-fluoro-3-methoxyphenyl, 2,4- difluorophenyl, 3,4-difluorophenyl, 3-chloro-4-fluorophenyl, 4-chloro-3-fluorophenyl, 3,4-ethylenedioxyphenyl, 2-naphthyl, 2,3-dichlorophenyl, 3,4-dichlorophenyl, 3,4-methylenedioxyphenyl, most preferably 2,3-dichlorophenyl, 3,4-dichlorophenyl or 3,4-methylenedioxyphenyl.

Within the above preferred, more preferred group and particularly preferred groups, an even more preferred group of compounds is that wherein:

(i) $Ar^2$ is pyrimidin-2-yl ring optionally substituted with alkyl or a phenyl ring which is optionally substituted with one, two, or three substituents selected from alkyl, alkoxy, alkylthio, halo, alkenyl, amino, monosubstituted amino, disubstituted amino or benzofuran-2-yl, preferably a pyrimidin-2-yl ring optionally substituted with a phenyl ring which is optionally substituted with one, two, or three substituents selected from methyl, methoxy, methylthio, chloro, fluoro, vinyl, dimethylamino, most preferably pyrimidin-2-yl, 5-(benzofuran-2-yl)pyrimidin-2-yl, 5-phenylpyrimidin-2-yl, 5-(4-methoxyphenyl)-pyrimidin-2-yl, 5-(3,4-dimethoxyphenyl)pyrimidin-2-yl, 5-(4-dimethylaminophenyl)-pyrimidin-2-yl, 5-(4-methylphenyl)pyrimidin-2-yl, 5-(4-methylthiophenyl)pyrimidin-2-yl, 5-(4-vinylphenyl)pyrimidin-2-yl, or 5-(4-fluorophenyl)pyrimidin-2-yl.

(ii) Another particularly preferred group of compounds is that wherein:

$Ar^2$ is a pyrazolyl ring optionally substituted with one or two substituents selected from alkyl or phenyl which is optionally substituted with a group selected from alkyl, halo, or —$SO_2R$ (where R is alkyl, alkoxy, amino, mono- or disubstituted amino), preferably pyrazol-4-yl optionally substituted with one or two substituents selected from methyl or phenyl which is optionally substituted with a group selected from methyl, 2-propyl, fluoro, chloro, methoxy, or —$SO_2NH_2$, more preferably 1-(4-methylphenyl)-pyrazol-4-yl, 1-(4-methoxyphenyl)pyrazol-4-yl, 1-[4-(2-propyl)phenyl]pyrazol-4-yl, 1-(4-aminosulfonylphenyl)pyrazol-4-yl or 1-(4-fluorophenyl)pyrazol4-yl.

(iii) A third particularly preferred group of compounds is that wherein:

$Ar^2$ is:
pyridyl, preferably 4-pyridyl;
quinoxaline, preferably quinoxalin-2-yl; or
9H-1,3,4,9-tetraazafluorene, preferably 9H-1,3,4,9-tetraaza-fluor-2-ene.

(e) A fifth more preferred group of compounds in group (I) is that wherein:
Z is —N—; and
B —$CH_2N$—.

(II) Another preferred group of compounds is that wherein:
Z is —N—;
$R^1$ is hydrogen; and
A is —NHCONH—.

Within this preferred group (II), a more preferred group of compounds is that wherein:
B is a bond.

Within these preferred and more preferred groups, a particularly preferred group of compounds is that wherein:
The stereochemistry at the C-3 carbon of the pyrrolidine ring is (S);
Q is a straight or branched alkylene chain of 1 to 3 carbon atoms, preferably —$CH_2$—, —$CH(CH_3)$—, —$C(CH_3)_2$—;

$Ar^1$ is a naphthyl or a phenyl ring which is optionally substituted with one, two or three substituents, selected from alkyl, cyano, nitro, halo, methylenedioxy, ethylenedioxy, alkoxy or phenoxy; preferably one or two substituents methyl, chloro, fluoro, bromo, methylenedioxy; more preferably 3-chlorophenyl, 4-chlorophenyl, 4-fluoro-3-methoxy-phenyl, 2,4-difluorophenyl, 3,4-difluorophenyl, 3-chloro-4-fluorophenyl, 4-chloro-3-fluorophenyl, 3,4-ethylenedioxyphenyl, 2-naphthyl, 2,3-dichlorophenyl, 3,4-dichloro-phenyl, 3,4-methylenedioxyphenyl, most preferably 2,3-dichlorophenyl, 3,4-dichloro-phenyl or 3,4-methylenedioxyphenyl; and $Ar^2$ is an aryl ring, preferably a phenyl ring which is optionally substituted with one, two, or three substituents selected from alkyl or alkoxy, preferably a phenyl ring optionally substituted with one or two substituents selected from methyl or methoxy; more preferably phenyl, 3-methylphenyl, 4-methylphenyl, 3-methoxyphenyl or 4-methoxyphenyl.

Particularly preferred compounds of the invention are:

N-[1-(2,3-dichlorobenzyl)pyrrolidin-3-(RS)-ylmethyl]-2-[5-(4-methoxyphenyl)pyrimidin-2-ylsulfanyl]acetamide.

N-[1-(2,3-dichlorobenzyl)pyrrolidin-3-(RS)-ylmethyl]-3-[5-(4-methoxyphenyl)pyrimidin-2-yl]propionamide.

N-[1-(2,3-dichlorobenzyl)pyrrolidin-3-(RS)-ylmethyl]-3-[5-(4-methoxyphenyl)pyrimidin-2-yl]propionamide hydrochloride salt.

N-[1-(3,4-dichlorobenzyl)pyrrolidin-3-(RS)-ylmethyl]-2-[5-(4-methoxyphenyl)pyrimidin-2-ylsulfanyl]acetamide.

N-[1-(3,4-methylenedioxybenzyl)pyrrolidin-3-(RS)-ylmethyl]-2-[5-(4-methoxyphenyl)pyrimidin-2-ylsulfanyl]acetamide hydrochloride salt.

N-[1-(2,3-dichlorobenzyl)pyrrolidin-3-(RS)-ylmethyl]-3-[5-(3,4-dimethoxyphenyl)pyrimidin-2-yl]propionamide.

N-[1-(2,3-dichlorobenzyl)pyrrolidin-3-(RS)-ylmethyl]-2-[5-(4-methoxyphenyl)pyrimidin-2-ylsulfanyl]acetamide hydrochloride salt.

N-[1-(2,3-dichlorobenzyl)pyrrolidin-3-(RS)-ylmethyl]-2-[5-(4-methoxyphenyl)pyrimidin-2-yloxy]acetamide.

N-[1-(2,3-dichlorobenzyl)pyrrolidin-3-(RS)-ylmethyl]-3-[5-(4-biphenyl)-pyrimidin-2-yl]propionamide.

N-1-(3,4-Dichlorobenzyl)-1-methyl-3-(RS)-{[2-(5-phenylpyrimidin-2-ylsulfanyl)-acetylamino]methyl}pyrrolidinium iodide.

N-[1-(3,4-dichlorobenzyl)pyrrolidin-3-(RS)-ylmethyl]-3-[5-(3,4-dimethoxyphenyl)pyrimidin-2-yl]propionamide.

N-[1-(3-chlorobenzyl)pyrrolidin-3-(RS)-ylmethyl]-3-[5-(4-methoxybenzyl)-pyrimidin-2-yl]propionamide.

N-[1-(3,4-methylenedioxybenzyl)pyrrolidin-3-(RS)-ylmethyl]-2-[5-phenyl-pyrimidin-2-ylsulfanyl]acetamide.

N-[1-(3,4-dichlorobenzyl)pyrrolidin-3-(RS)-ylmethyl]-2-[5-(3,4-dimethoxyphenyl)pyrimidin-2-yloxy]acetamide.

N-[1-(2,3-dichlorobenzyl)pyrrolidin-3-(RS)-ylmethyl]-2-[5-(4-methylthiophenyl)pyrimidin-2-yloxy]acetamide.

N-[1-(3-chlorobenzyl)pyrrolidin-3-(RS)-ylmethyl]-2-[5-(4-methoxyphenyl)-pyrimidin-2-ylsulfanyl]acetamide.

N-[1-(2,3-dihydrobenzofuran-5-yl)pyrrolidin-3-(RS)-ylmethyl]-2-[5-(4-methoxyphenyl)pyrimidin-2-ylsulfanyl]acetamide.

N-[1-(2,3-dichlorobenzyl)pyrrolidin-3-(RS)-ylmethyl]-2-[5-phenylpyrimidin-2-ylsulfanyl]acetamide.

N-[1-(3,4-methylenedioxybenzyl)pyrrolidin-3-(RS)-ylmethyl]-3-[5-(4-methoxyphenyl)pyrimidin-2-yl]propioamide hydrochloride salt.

N-[1-(2,3-dichlorobenzyl)pyrrolidin-3-(RS)-ylmethyl]-2-[5-(4-methoxyphenyl)pyrimidin-2-yloxy]acetamide.

N-[1-(3,4-dichlorobenzyl)pyrrolidin-3-(RS)-ylmethyl]-3-[5-(4-methoxyphenyl)pyrimidin-2-yl]propioamide hydrochloride salt.

N-[1-(2,3-dichlorobenzyl)pyrrolidin-3-(S)-ylmethyl]-2-(3-fluoro-4-hydroxyphenyl)acetamide.

N-[1-(2,3-dichlorobenzyl)pyrrolidin-3-ylmethyl]-2-(3-acetylaminophenyl)acetamide.

GENERAL SYNTHETIC SCHEME

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Enika-Chemie, or Sigma (St. Louis, Mo., USA), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), Butt Park Ltd., (Dist. Interchim, Montlucon Cedex, France) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), March's Advanced Organic Chemistry, (John Wiley and Sons, 1992), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Synthesis of Compounds of Formula (I)

In general, compounds of Formula (I) where Z is —N— and A, B, $R^1$, $R^2$, $R^3$, $R^4$, $R^5$, $R^6$, Q, $Ar^1$ and $Ar^2$ are as defined in the Summary of the Invention are prepared from 3-aminomethylpyrrolidines (Ia) or (Ib) or 3-hydroxymethylpyrrolidine (Ic) as shown in FIG. 1 below. A compound of Formula (I) where Z is —N— can be converted to a corresponding compound of Formula (I) where —N$^+$R—X$^-$, if desired, by alkylation with an alkylating agent RX where R is as defined in the Summary of the Invention and X is a leaving group.

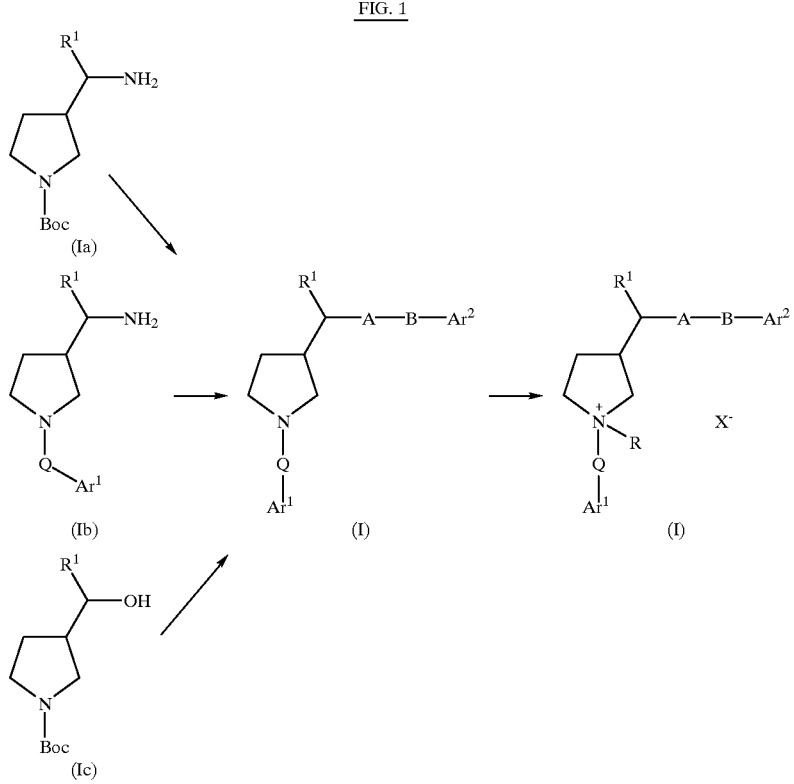

FIG. 1

Synthesis of compounds of Formulae (Ia), (Ib) and (Ic) and their conversion to compounds of Formula (I) are described in detail in Schemes A–D and E–K, respectively.

SYNTHESIS OF COMPOUNDS OF FORMULAE (Ia), (Ib) AND (Ic)

Synthesis of Compounds of Formula (Ia)

Scheme A

A compound of Formula (Ia) where $R^1$ is hydrogen is prepared as shown in Scheme A below.

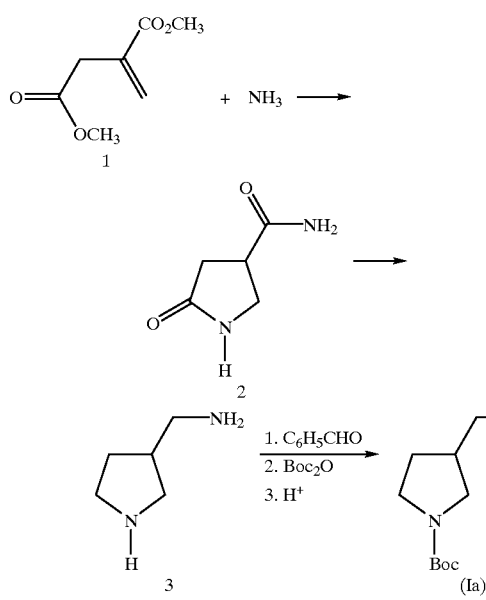

Treatment of commercially available dimethyl itaconate of formula 1 with ammonia gives 4-aminocarbonyl-2-pyrrolidinone 2. Reduction with a suitable reducing agent (such as lithium aluminum hydride, diborane, and the like) in an aprotic organic solvent such as tetrahydrofuran gives 3-aminomethylpyrrolidine 3. Protection of the primary amino group as the benzylimine, followed by treatment with di-tert-butyl dicarbonate in the presence of a base (e.g., sodium hydroxide, sodium carbonate, triethylamine, and the like) gives 3-[(benzylideneaminomethyl)-1-tert-butoxycarbonylpyrrolidine which upon a mild acidic workup provides the desired 3-aminomethyl-1-tert-butoxycarbonylpyrrolidine of Formula (Ia). Compound (Ia) is then converted to a compound of Formula (I) as described in Schemes E–K below.

Scheme B

A compound of Formula (Ib) where $R^1$ is hydrogen can be prepared as described in Scheme B below.

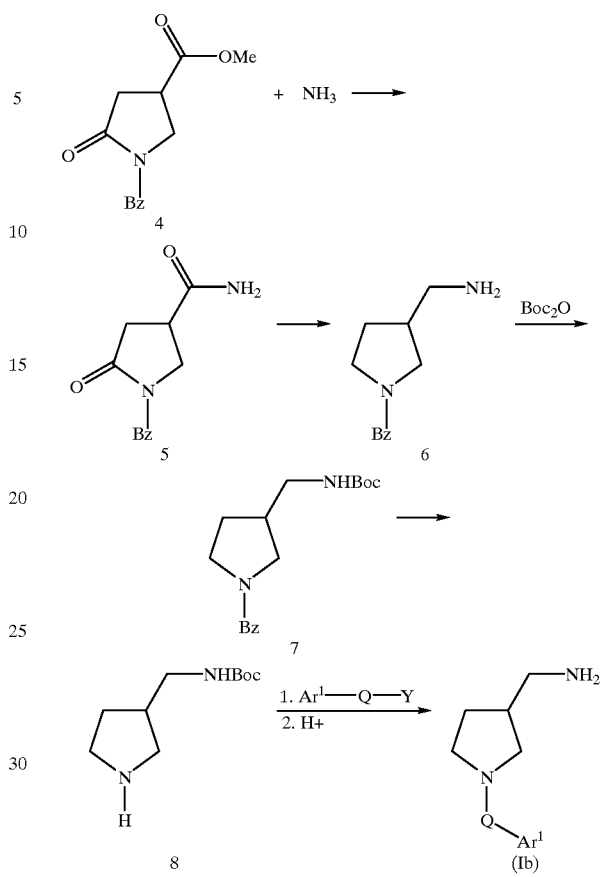

Treatment of 1-benzyl-5-oxo-pyrrolidine3-carboxylic acid methyl ester 4 with ammonia provides 3-aminocarbonyl-1-benzyl-2-pyrrolidinone 5. Reduction of 5 with a suitable reducing agent (such as lithium aluminum hydride, diborane and the like) in an aprotic organic solvent such as tetrahydrofuran gives 3-aminomethyl-1-benzylpyrrolidine 6. Protection of the primary amino group as the tert-butoxycarbonyl, followed by debenzylation under standard hydrogenation reaction conditions provides 3-(tert-butoxycarbonylaminomethyl)pyrrolidine 8. Compound 8 is then converted to a compound of Formula (Ib) by reacting it with a compound of formula $Ar^1$—Q—Y where Y is an aldehyde (—CHO) or a keto (—C(O)R where R is alkyl) group, followed by removal of the Boc group. The reaction of 8 with $Ar^1$—Q—Y is carried out under reductive amination reaction conditions i.e., in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like).

In general, compounds of formula $Ar^1$—Q—Y are commercially available. For example, benzaldehyde, acetophenone, 3,5-dichlorobenzaldehyde, 2-phenylpropionaldehyde, and the like are commercially available. Compound (Ib) is then converted to a compound of Formula (I) as described in Schemes E–K below.

Scheme C

Alternatively, a compound of Formula (Ib) where $R^1$ is hydrogen is prepared as shown in Scheme C below.

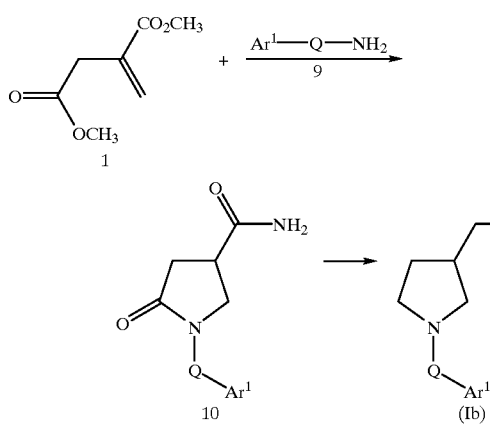

Treatment of commercially available dimethyl itaconate of formula 1 with an amine of formula 9 (where Ar¹ is as defined in the Summary of the Invention) provides a compound of formula 10 which is converted to a compound of Formula (Ib) as described above. Compounds of formula 9 such as benzylamine, 3,4-dichlorobenzylamine, phenethylamine, and the like are commercially available.

Preparation of Compounds of Formula (Ic)

Scheme D

A compound of Formula (Ic) where R¹ is hydrogen is prepared as shown in Scheme D below.

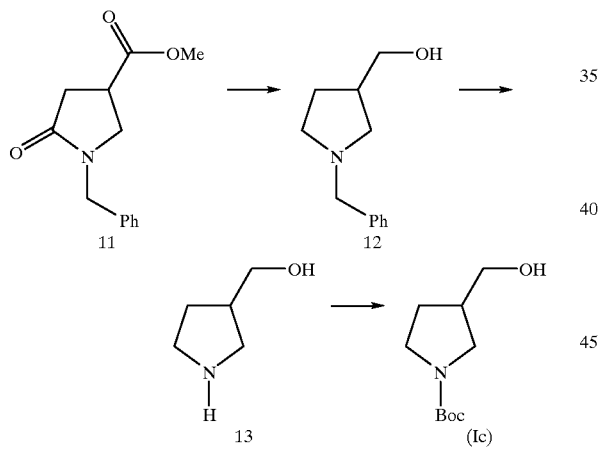

Reduction of 1-benzyl-5-oxo-pyrrolidine-3-carboxylic acid methyl ester 11 with a suitable reducing agent (such as lithium aluminum hydride, borane, and the like) gives N-benzyl-3-hydroxymethylpyrrolidine 12. Removal of the benzyl group under catalytic hydrogenation reaction conditions followed by reaction of 3-hydroxymethylpyrrole 13 with di-tert-butyl dicarbonate in the presence of a base (e.g., sodium hydroxide, sodium carbonate, and the like) gives N-tert-butoxycarbonyl-3-hydroxymethylpyrrolidine of Formula (Ic). Compound (Ic) is then converted to a compound of Formula (I) as shown below.

Synthesis of Compounds of Formula (I) from Compounds of Formulae I(a–c)

Compounds of Formula (I) where Z is —N— and R¹ is hydrogen are prepared from compounds of Formulae I(a–c) as described in Schemes E–K below.

Scheme E

Compounds of Formula (I) where A is —N(R²)C(O)— where R² is hydrogen are prepared from a compound of Formula (Ia) or (Ib) as described in Scheme E below.

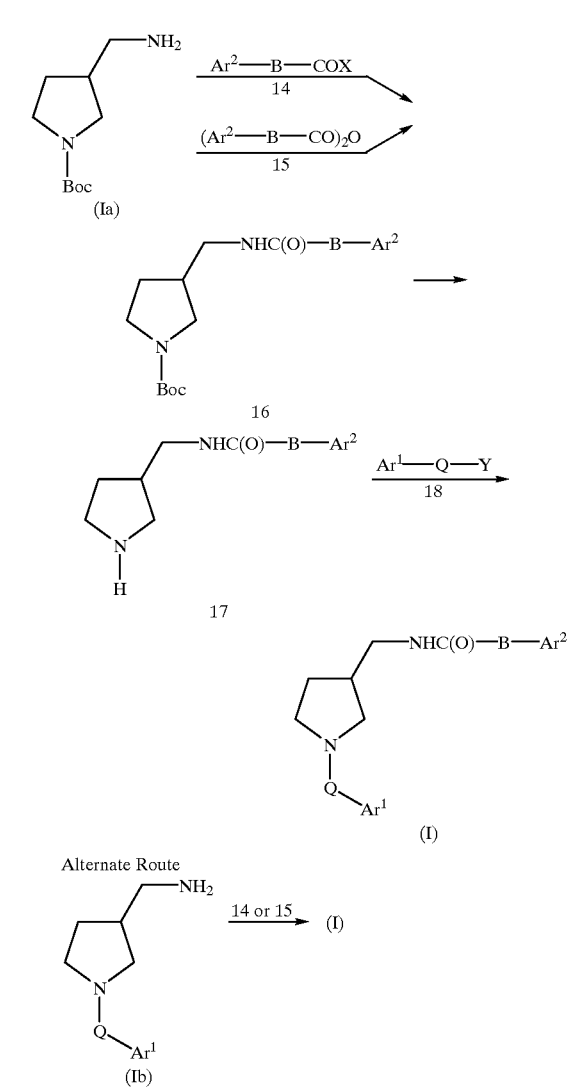

Reaction of a compound of Formula (Ia) with a compound of formula 14 where B is as defined in the Summary of the Invention and X is a leaving group under acylating conditions such as a halo (particularly Cl or Br) or a hydroxy group gives a compound of formula 16. The reaction conditions employed for the preparation of 16 depend on the nature of the X group. If X is a hydroxy group, the reaction is carried out in the presence of a suitable coupling agent (e.g., N,N-dicyclohexylcarbodiimide, 1-(3-dimethylamino-propyl)-3-ethylcarbodiimide, and the like). If X is a halide the reaction is carried out in the presence of a non-nucleophilic organic base (e.g., triethylamine or pyridine, preferably pyridine). Suitable organic solvent are methylene chloride, tetrahydrofuran, and the like.

Iternatively, 16 can be prepared by heating (Ia) with an acid anhydride. Suitable solvents for the reaction are tetrahydrofuran, dioxane, and the like. Compounds of formula 14 such as 4-(2,5-dimethylphenyl)-4-oxobutyric acid, 4-(acetylphenoxy)acetic acid, N-phenylsulfonylglycine, 2-(6-methoxynaphth-2-yl)-2-methylacetic acid, 3-benzenesulfonyl-propionic acid, 4-(thiophen-2-ylpyrazol-1-yl)acetic acid, 2-(1-acetylnaphth-2-yloxy)-2-methylacetic acid, 2-(4-methyl[1,2,3]thiadiazol-5-ylsulfanyl)acetic acid, 2-(quinoxalin-2-ylsulfanyl)acetic acid are commercially available.

Treatment of 16 with an aqueous acid or anhydrous acid such as hydrochloric acid or trifluoroacetic acid in dichloromethane gives a compound of formula 17 which is then converted to a compound of Formula (I) by procedures well known in the art. Some such procedures are described below.

A compound of Formula (I) can be prepared:

(i) by reacting a compound of Formula 17 with a compound of formula 18 where Y is an aldehyde (—CHO) or a keto (—C(O)R where R is alkyl) group as described previously; or (ii) by reacting a compound of formula a compound of Formula 17 with a compound of formula 18 where Y is a leaving group under alkylating conditions such as halo (e.g., chloro, bromo or iodo) or sulfonyloxy group (e.g., methylsulfonyloxy or 4-methylphenylsulfonyloxy or trifluoromethylsulfonyloxy). The reaction is carried out in the presence of a base such as sodium carbonate, sodium hydride, triethylamine and the like. Suitable solvents are aprotic organic solvents such as tetrahydrofuran, N,N-dimethylformamide, and the like.

In general, compounds of formula 18 where Y is an aldehyde or ketone group are commercially available. For example, benzaldehyde, acetophenone, 3,5-dichlorobenzaldehyde, 2-phenylpropionaldehyde, and the like are commercially available. Aralkyl halides such as benzyl bromide, 3,4-dichlorobenzyl bromide, and the like are also commercially available. Others can be prepared from suitable starting materials such as phenylacetic acid, phenylpropanol, benzyloxyethanol, 3,5-dichlorobenzaldehyde, 2-phenylpropionaldehyde, etc., by reducing the aldehyde, ketone or carboxy group to an alcohol, followed by treatment with a suitable halogenating agent (e.g., thionyl chloride, thionyl bromide, carbon tetrabromide in the presence of triphenylphosphine, and the like) or sulfonylating agent (e.g., methylsulfonyl chloride, para-toluenesulfonyl chloride and triflic anhydride) respectively. Suitable aldehyde, ketone or carboxy reducing agents include lithium aluminum hydride, borane and the like.

Alternatively, a compound of Formula (I) can be prepared directly by reacting a compound of Formula (Ib) with a compound of formula 14 or 15 utilizing the reaction conditions described above.

Scheme F

Compounds of Formula (I) where Z is —N—, $R^1$ is hydrogen and A is —N($R^2$)C(O)N($R^3$)— or —N($R^2$)C(S)N($R^3$)— are prepared as described in Scheme F below:

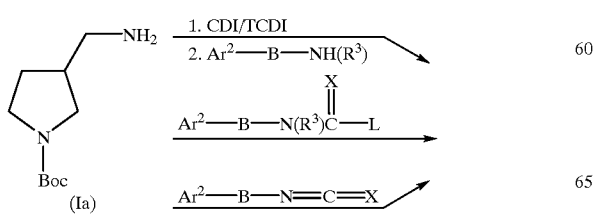

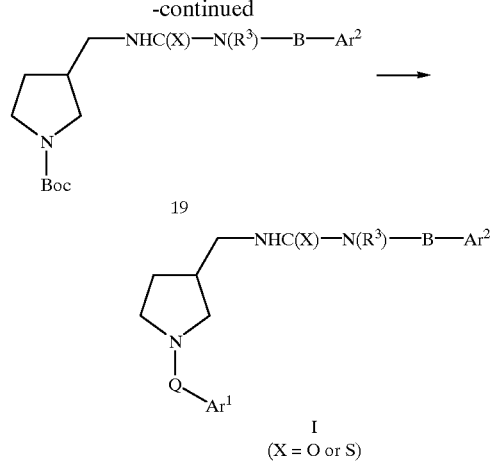

A compound of Formula (I) where A is a urea/thiourea group can be prepared from a compound of Formula (Ia) by first preparing a compound of formula 19 either:

(i) by reacting a compound of Formula (Ia) with an activating agent such as carbonyl diimidazole/thiocarbonyl diimidazole, followed by nucleophilic displacement of the imidazole group with a primary or secondary amine. The reaction occurs at ambient temperature. Suitable solvents include polar organic solvents (e.g., tetrahydrofuran, dioxane and the like);

(ii) by reacting a compound of Formula (Ia) with a carbamoyl/thiocarbamoyl halide. The reaction is carried out in the presence of a non-nucleophilic organic base. Suitable solvents for the reaction are dichloromethane, 1,2-dichloroethane, tetrahydrofuran or pyridine; or (iii) by reacting a compound of Formula (Ia) with an isocyanate/isothiocyanate in an aprotic organic solvent (e.g., benzene, tetrahydrofuran, dimethylformamide and the like).

Compound 19 is then converted to a compound of Formula (I) as described in Scheme E above.

Compound (I) can be prepared directly from a compound of Formula (IIb) by carrying out the steps (i)–(iii) above.

Scheme G

Compounds of Formula (I) where Z is —N—, $R^1$ is hydrogen and A is —N($R^2$)$SO_2$— where $R^2$ is hydrogen are prepared as described in Scheme G below:

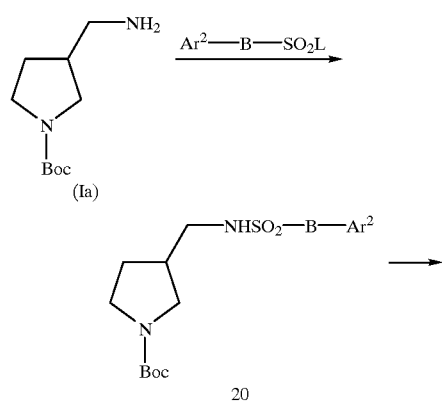

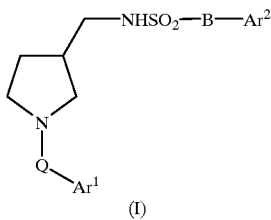

(I)

A compound of Formula (I) where A is a sulfonamido group can be prepared by reacting a compound of Formula (Ia) with a sulfonyl halide, utilizing the reaction conditions described in method (ii) of Scheme D above to give a compound of formula 20 which is then converted to a compound of Formula (I) as described in Scheme E above.

Sulfonyl halides are commercially available or may be prepared by methods such as those described in (1) Langer, R. F.; *Can. J. Chem.* 61, 1583–1592, (1983); (2) Aveta, R.; et. al.; *Gazetta Chimica Italiana*, 116, 649–652, (1986); (3) King, J. F. and Hillhouse, J. H.; *Can. J. Chem.*; 54, 498, (1976); and (4) Szymonifka, M. J. and Heck, J. V.; *Tet. Lett.*; 30, 2869–2872, (1989).

Scheme H

Compounds of Formula (I) where Z is —N—, $R^1$ is hydrogen and A is —N($R^2$)$SO_2$N($R^3$)— where $R^2$ is hydrogen are prepared as described in Scheme H below:

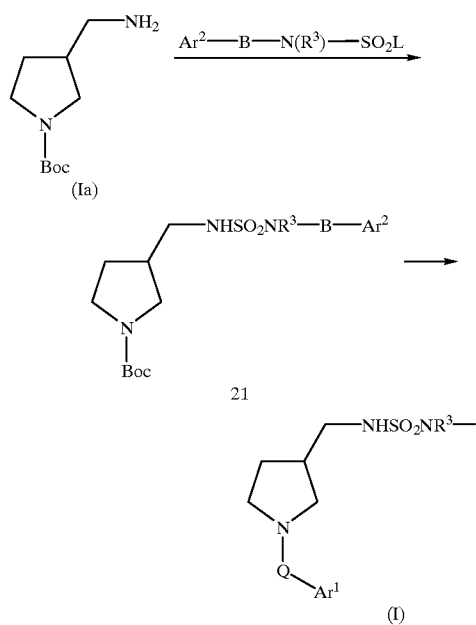

(I)

A compound of Formula (I) where A is a sulfamide group can be prepared by reacting a compound of Formula (Ia) with a sulfamoyl halide, utilizing the reaction conditions described in method (ii) of Scheme E above to give a compound of formula 21 which is then converted to a compound of Formula (I) as described in Scheme C above. Sulfamoyl halides are commercially available or may be prepared by methods such as those described in Graf, R; German Patent, 931225 (1952) and Catt, J. D. and Mailer, W. L; *J. Org. Chem.*, 39, 566–568, (1974).

Scheme I

Compounds of Formula (I) where Z is —N—, $R^1$ is hydrogen and A is —N($R^2$)C(O)O— where $R^2$ is hydrogen are prepared as described in Scheme I below:

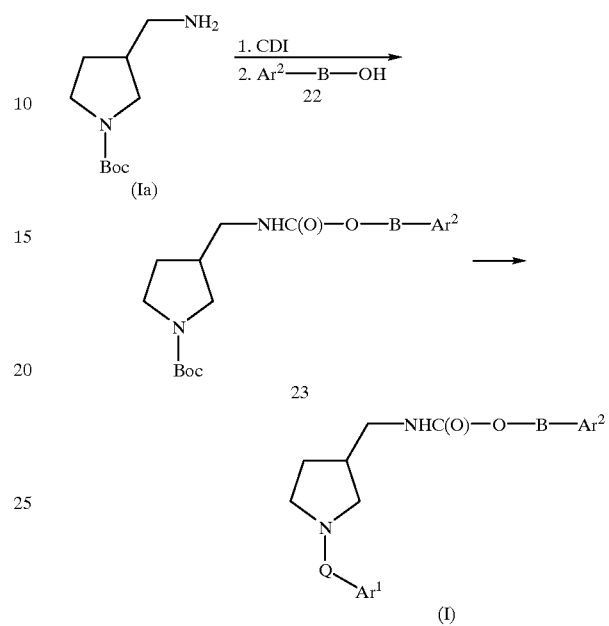

A compound of Formula (I) where A is a carbamate group can be prepared by first converting a compound of Formula (Ia) to a compound of formula 23 by reacting it with an activating agent such as carbonyl diimidazole, followed by nucleophilic displacement of the imidazole group with an alcohol of formula 22. The reaction occurs at ambient temperature. Suitable solvents include polar organic solvents (e.g., tetrahydrofuran, dioxane and the like). A compound of formula 24 which is then converted to a compound of Formula (I) as described in Scheme E above.

Alcohols of formula 22 such as benzyl alcohol, 3-benzylpropanol, and the like are commercially available.

Scheme J

Compounds of Formula (I) where Z is —N—, $R^1$ is hydrogen and A is —OC(O)N($R^3$)— are prepared as described in Scheme J below:

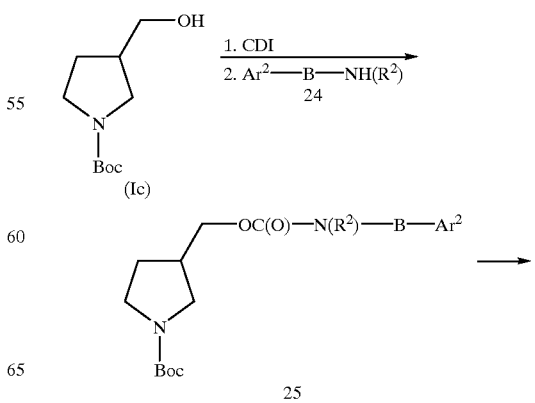

-continued

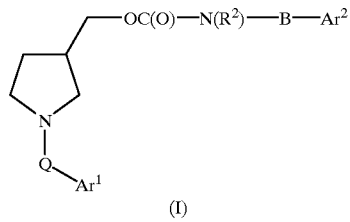

A compound of Formula (I) where A is an inverse carbamate group can be prepared by first converting a compound of Formula (Ic) to a compound of formula 25 by reacting it with an activating agent such as carbonyl diimidazole, followed by nucleophilic displacement of the imidazole group with an amine of formula 24. The reaction occurs at ambient temperature. Suitable solvents include polar organic solvents (e.g., tetrahydrofuran, dioxane and the like). A compound of formula 25 which is then converted to a compound of Formula (I) as described in Scheme E above.

It will be recognized by one skilled in the art that above procedures can be utilized to prepare compounds of Formula (I) directly from a compound of Formula (Ib).

Synthesis of a Compounds of Formula (I) where Z is —N— to a Corresponding Compound of Formula (I) where Z is —N$^+$R—X$^-$ Scheme K A compound of Formula (I) where Z is —N$^+$R— can be prepared from a corresponding compound of Formula (I) as shown in Scheme K below.

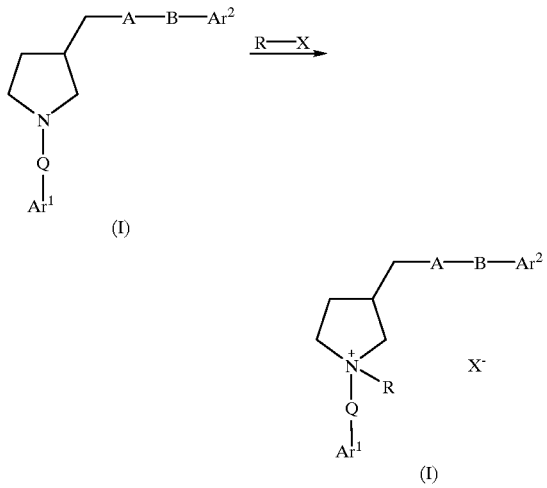

A compound of Formula (I) is converted to a corresponding compound of Formula (I) where Z is —N$^+$R— where R is an alkyl, haloalkyl, aralkyl, hydroxyalkyl, carboxyalkyl, alkoxycarbonylalkyl, or cyanoalkyl group and X$^-$ is iodide, by stirring it in neat alkyl iodide such as methyl iodide, ethyl iodide, and the like.

The iodide salt can be converted to its corresponding chloride salt by utilizing a suitable ion exchange resin such as Dowex 1x8-50.

Utility, Testing and Administration

General Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Testing

The CCR-3 antagonistic activity of the compounds of this invention was measured by in vitro assays such as ligand binding and chemotaxis assays as described in more detail in Examples 14, 15 and 16. In vivo activity was assayed in the Ovalbumin induced Asthma in Balb/c Mice Model as described in more detail in Example 17.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.01–20 mg per kilogram body weight of the recipient per day; preferably about 0.1–10 mg/kg/day. Thus, for administration to a 70 kg person, the dosage range would most preferably be about 7 mg to 0.7 g per day.

In general, compounds of this invention will be administered as pharmaceutical compositions by any one of the following routes: oral, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, liposomes, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices—nebulizer inhalers, metered-dose inhalers (MDI) and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

For liposomal formulations of the drug for parenteral or oral delivery the drug and the lipids are dissolved in a suitable organic solvent e.g. tert-butanol, cyclohexane (1% ethanol). The solution is lypholized and the lipid mixture is suspended in an aqueous buffer an allowed to form a liposome. If necessary, the liposome size can be reduced by sonification. (see, Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998)).

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 13.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 3-(RS)-aminomethyl-1-tert-butoxycarbonylpyrrolidine

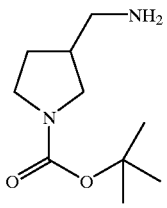

Step 1

Melted dimethyl itaconate (150 g, 0.95 mol) was added to an anhydrous solution of ammonia in methanol (7 M, 1000 mL, 7 mol) at room temperature. The reaction vessel was sealed with parafilm and vented with a needle. The solution was left to stand for 3 days, after which the solid was filtered and washed with cold methanol and dried under vacuum to yield pure 4-aminocarbonylpyrrolidin-2-one (150 g).

Step 2

To a stirred slurry of 4-aminocarbonylpyrrolidin-2-one (20 g, 156 mmol) in (100 mL) of cold (0° C.) dry tetrahydrofuran, in a 1 L flask under $N_2$, was added a solution of lithium aluminum hydride (12 g, 0.32 mmol) in dry tetrahydrofuran (350 mL) dropwise. Once addition was complete and hydrogen evolution had abated, the cooling bath was removed and the reaction mixture was heated at reflux temperature. After the reaction was complete, the reaction mixture was allowed to cool to room temperature and ether (300 mL) was added. Sufficient saturated $Na_2SO_4$ was added dropwise over 1 h to destroy excess hydride. Excess water was avoided so as to prevent two phases forming, as the diamine is highly water-soluble. The suspension was filtered over celite with copious washings with tetrahydrofuran and 15% methanol in tetrahydrofuran. The combined washings were concentrated on the rotovap and the pungent residue distilled under vacuum to yield pure 3-(RS)-aminomethylpyrrolidine as a colorless mobile oil (7.6 g).

Step 3

Benzaldehyde (5.3 g, 50 mmol) was added to a solution of 3-aminomethyl-pyrrolidine (5.0 g, 50 mmol) in toluene (anhydrous, 100 mL) in a 250 mL flask at room temperature under $N_2$. A Dean-Stark apparatus and condenser were fitted and the reaction mixture was heated at reflux for 4 h. The reaction mixture was cooled to room temperature and di-tert-butyldicarbonate (5.3 g, 50 mmol) was added portion-wise and the resulting solution is stirred at room temperature overnight. The reaction mixture was concentrated on the rotavap and the residue was diluted with 1 M NaHSO₄ (80 mL, 80 mmol, 1.6 equiv.) and stirred vigorously for 2 h. The reaction mixture was washed with ether to remove unwanted organic byproducts, then basified with 1 M NaOH to pH 7. Further extraction with either ether or ethyl acetate removed additional unwanted byproducts. The aqueous solution was then made strongly basic (pH 12) with 1 M NaOH and extracted with ethyl acetate. The organic layer was washed with brine, dried with Na₂SO₄, then concentrated to give the 3-(RS)-aminomethyl-1-tert-butoxycarbonyl-pyrrolidine as a colorless oil (80–90%), which was used directly without further purification.

Example 2

Synthesis of 3-(S)-aminomethyl-1-tert-butoxycarbonylpyrrolidine

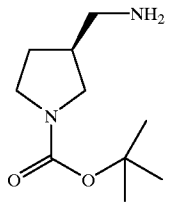

Step 1

(S)-pyrrolidinol (30 g, 0.34 mol) was dissolved in a mixture of water/dioxane (400 mL/300 mL) and N,N-diisopropylethylamine (120 mL, 0.69 mol, 2 equiv.) was added. This reaction mixture was cooled to 0° C. and di-tert-butyldicarbonate (90 g, 0.41 mol, 1.2 equiv.) in solution in dioxane (100 mL) was added slowly. The resulting mixture was stirred at 0° C. for 1 h then at room temperature for 8 h. The reaction mixture was then partitioned between diethyl ether and water. The aqueous phase was acidified to pH 3.0 with 1 M HCl and extracted with ethyl acetate. The organic phases were combined and washed with a brine solution. The resulting organic layer was dried over magnesium sulfate, filtered and concentrated to give, after purification by flash chromatography (methanol/CH₂Cl₂: 15/85) (S)-1-(tert-butoxycarbonylamino)-3-hydroxypyrrolidine as a white solid (40 g).

Step 2

(S)-1-(tert-Butoxycarbonylamino)-3-hydroxypyrrolidine (40 g, 0.21 mol) was dissolved in anhydrous methylene chloride (400 mL), in the presence of N,N-diisopropylethylamine (73 mL, 0.42 mol, 2 equiv.) and cooled using an ice bath. This solution was treated with methanesulfonyl chloride (18 mL, 0.23 mol, 1.1 equiv.) over a 30 min. period and was then allowed to stir at room temperature for 4 h. The solution was concentrated and the residue dissolved in ethyl acetate (250 mL). The resulting organic solution washed with 5% NaHCO₃ and then with brine. The organic extract was dried over magnesium sulfate, filtered and concentrated to give (S)-1-(tert-butoxycarbonyl-amino)-3-methanesulfonyloxypyrrolidine as a dark oil (39 g) which was used directly without further purification.

Step 3

(S)-1-(tert-Butoxycarbonylamino)-3-methanesulfonyloxypyrrolidine (39 g, 0.15 mol) was dissolved in acetonitrile (250 mL) and tetra-n-butylammonium cyanide (75 g, 0.28 mol, 1.9 equiv.) was added. The resulting mixture was heated at 65° C. for 6 h and then cooled to room temperature. Saturated NaHCO₃ (500 mL) was added and the reaction mixture extracted with toluene (750 mL and 300 mL). The combined organic layers were washed with water and concentrated under reduced pressure to give a brown oil. This crude material was purified by flash chromatography with 20% ethyl acetate in hexane to give (S)-1-(tert-butoxycarbonylamino)-3-cyanopyrrolidine as a yellow oil (13.5 g).

Step 4

A solution of (S)-1-(tert-butoxycarbonylamino)-3-cyanopyrrolidine (13.5g, 67 mmol) in 50 mL of 3% NH₄OH/methanol and Raney Nickel (0.5 g, 50% slurry in water) was pressurized to 40 psi under H₂ atmosphere. After stirring for 12 h at room temperature, the reaction mixture was filtered through a pad of Celite and the residue was washed with 100 mL of methanol. The filtrate was concentrated to dryness to give an oil (S)-1-(tert-butoxycarbonylamino)-3-aminomethylpyrrolidine (10 g).

Proceeding as described above, but substituting (S)-pyrrolidinol (1) with (R)-pyrrolidinol (1) gave (R)-1-(tert-butoxycarbonylamino)-3-aminomethylpyrrolidine.

Example 3

Synthesis of 3-(RS)-aminomethyl-1-(3,4-dichlorobenzyl)pyrrolidine

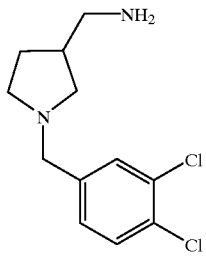

Step 1

Neat 3,4-dichlorobenzylamine (18 g, 114 mmol) was added to a solution of dimethyl itaconate (20 g, 114 mmol) in methanol (200 mL) at room temperature. The solution was stirred at for 48 h then concentrated in vacuo. The resulting solid was divided equally into two, one portion being treated with methanolic ammonia (7 M, 300 mL, 2.1 mol). The solution was vented with a needle and allowed to stand for 2 days. The slurry of solvent and product was concentrated further and filtered. The filter cake was washed with cold methanol to give pure 3-aminocarbonyl-1-(3,4-dichlorobenzyl)-pyrrolidin-2-one (18.5 g).

Step 2

A suspension of 3-aminocarbonyl-1-(3,4-dichlorobenzyl)pyrrolidin-2-one in dry tetrahydrofuran (150 mL) was added slowly to a solution of lithium aluminum hydride (4.9 g, 128 mmol, 2 equiv.) in tetrahydrofuran (100 mL) under N₂ at room temperature. The reaction mixture was heated at reflux overnight, diluted with ether, and quenched with brine. After 1 h of rapid stirring, the gray mixture was filtered through celite (ethyl acetate washings) and the filtrate was concentrated. Flash chromatography with CHCl₃/MeOH/NH₃ solution (200:25:1;) gave 3-(RS)-aminomethyl-1-(3,4-dichlorobenzyl)pyrrolidine compound as a colorless oil (6.2 g) which was >95% pure.

Example 4

Synthesis of N-[1-(2,3-dichlorobenzyl)pyrrolidin-3-(RS)-ylmethyl]-3-[5-(4-methoxyphenyl)pyrimidin-2-yl]propionamide Hydrochloride Salt

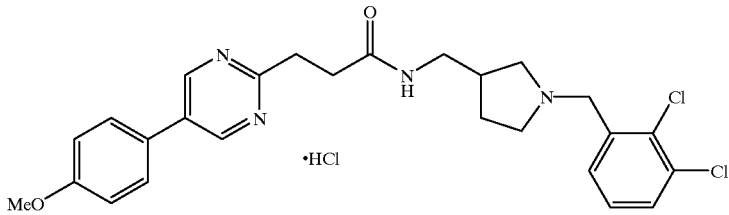

Step 1

Methyl 1-benzyl-5-oxo-3-pyrrolidinecarboxylate (50 g, 0.21 mol) was stirred in a solution of ammonia in methanol (7 M, 400 mL, 2.8 mol). After 2 days, the solution was concentrated with heating (50° C.) to about 300 mL at which point all solids remained dissolved. The reaction was then allowed to cool down and the resulting solid was filtered, washed with ether and dried to give 1-benzyl-5-oxo-pyrrolidine-3-carboxylic acid amide as colorless crystals (40 g).

Step 2

1-Benzyl-5-oxo-pyrrolidine-3-carboxylic acid amide (22 g, 0.1 mol) was added portionwise to a stirred solution of lithium aluminum hydride (9.5 g, 0.25 mol, 2.5 equiv.) in dry tetrahydrofuran (600 mL). After the initial effervescence had subsided, the reaction mixture was heated at reflux at room temperature for 24 h, at which time analysis of the reaction mixture by LCMS showed there was no starting material. The reaction mixture was quenched by dropwise addition of saturated sodium sulphate solution with stirring until no further effervescence was observed. The suspension was filtered through a celite plug, eluting with diethyl ether (200 mL). The solvent was remove to afford 3-(RS)-aminomethyl-1-benzylpyrrolidine as an oil (14.7 g) which was used directly without further purification.

Step 3

3-(RS)-Aminomethyl-1-benzylpyrrolidine (14.7 g, 80 mmol) was dissolved in methylene chloride (400 mL) with stirring. A solution of di-tert-butyl dicarbonate (16.8 g, 80 mmol, 1.0 equiv.) in methylene chloride (50 mL) was added dropwise and the reaction mixture was stirred overnight. The reaction mixture was concentrated and the residue was dissolved in diethyl ether (400 mL) and extracted with NaHSO$_4$ solution (1 M, 120 mL). The aqueous layer was basified to pH 12 with 1 M sodium hydroxide and extracted with ethyl acetate. The organic fractions were combined, washed with brine, dried over magnesium sulfate, and filtered. The organics were evaporated to afford 1-benzyl-3-(RS)-(N-tert-butoxycarbonylaminomethyl)pyrrolidine (22.5 g) which was used directly.

Step 4

1-Benzyl-3-(RS)-(N-tert-butoxycarbonylaminomethyl) pyrrolidine (22.2 g, 0.76 mol) was dissolved in a mixture of methanol and acetic acid (1:1, 100 mL) and added to a Parr flask charged with palladium on carbon (10%, 4 g) suspended in methanol and acetic acid (1:1, 100 mL). The flask was transferred to the Parr reduction apparatus and the suspension shaken under an atmosphere of hydrogen at 60 psi for 2 days. The reaction mixture was filtered through a celite plug, eluting with a mixture of methanol/methylene chloride. The solvent was concentrated and the residue co-evaporated with toluene to afford 3-(RS)-(N-tert-butoxycarbonylaminomethyl)pyrrolidine as a colorless oil which was used directly.

Step 5

Sodium triacetoxyborohydride (3.2 g, 15 mmol, 1.5 equiv.) was added in one portion to a stirred solution of 3-(RS)-(N-tert-butoxycarbonylaminomethyl)pyrrolidine (2.0 g, 10 mmol) and 2,3-dichlorobenzaldehyde (1.9 g, 11 mmol, 1.1 equiv.) in dichloroethane (60 mL) at room temperature. The suspension was stirred overnight, then concentrated in vacuo. The residue was diluted with ether and quenched with 1 M hydrochloric acid. The aqueous phase was basified with 4 M sodium hydroxide to pH 12, then extracted with ethyl acetate. The organic extracts were combined and washed with brine, then dried over sodium sulfate and concentrated. Flash chromatography of the residue afforded 3-(RS)-(N-tert-butoxycarbonylaminomethyl)-1-(2,3-dichlorobenzyl)-pyrrolidine as a colorless oil (2.9 g). The oil was taken up into methylene chloride (30 mL) and treated with neat trifluoroacetic acid (5 mL). After 1 h, the volatile components were removed on a vacuum pump, then concentrated further under high vacuum to give 3-(RS)-aminomethyl-1-(2,3-dichlorobenzyl)pyrrolidine which was used directly without further purification.

Step 6

A solution of sodium ethoxide (21% wt/vol in ethanol, 10 mL, 30 mmol, 3 equiv.) was added in one portion to a suspension of 2-(4-methoxyphenyl)trimethinium perchlorate (3.3 g, 9.8 mmol) [see, Jutz, C.; Kirchlechner, R.; Seidel, H., Chem. Ber. 102, 2301, (1969)] and 4-amidinobutanoic acid mono HCl (1.5 g, 9.8 mmol) [see, McElvain, S. M.; Schroeder, J. P., J. Am. Chem. Soc., 71, 40, (1949)] in absolute ethanol (40 mL). The reaction mixture was heated at reflux for 12 h, then cooled to room temperature. The suspension was concentrated, diluted with water, and washed with ether. The aqueous phase was then made acidic with citric acid (10 g). The precipitates were filtered, washed with water and ether, and dried under high vacuum to yield 3-[4-(4-methoxyphenyl)-pyrimidin-2-yl]propanoic acid (1.85 g) as an off-white solid.

Step 7

1-(3-Dimethylaminopropyl)-3-ethylcarbodiimide hydrochloride (0.29 g, 1.5 mmol, 1.5 equiv.) was added to a suspension of 3-[4-(4-methoxyphenyl)pyrimidin-2-yl]-propanoic acid (0.26 g, 1.0 mmol, 1.0 equiv.), 3-(RS)-aminomethyl-1-(2,3-dichlorobenzyl)-pyrrolidine (0.26 g, 1.0 mmol), 1-hydroxybenzotriazole hydrate (0.20 g, 1.5 mmol, 1.5 equiv.), and diisopropylethylamine (0.44 mL, 2.5 mmol, 2.5 equiv.) in chloroform (2 mL). After stirring overnight at room temperature, the reaction mixture was diluted with ethyl acetate, washed sequentially with 1 M sodium hydroxide, water, 1 M hydrochloric acid, water and brine, then dried over sodium sulfate and concentrated. The residue was purified by flash chromatography (0→10% methanol in methylene chloride). Clean fractions containing the desired product were combined and concentrated, diluted with dioxane and treated with 4 M HCl (0.2 mL) in dioxane. The solution was concentrated under high vacuum to give N-(1-(2,3-dichlorobenzyl)-pyrrolidin-3-(RS)-ylmethyl)-3-(5-(4-methoxyphenyl)pyrimidin-2-yl) propionamide as the HCl salt (185 mg).

Example 5

Synthesis of N-[1-(2,3-dichlorobenzyl)pyrrolidin-3-(RS)-ylmethyl]-3-[5-(4-nitrophenyl)pyrimidin-2-yl]propionamide

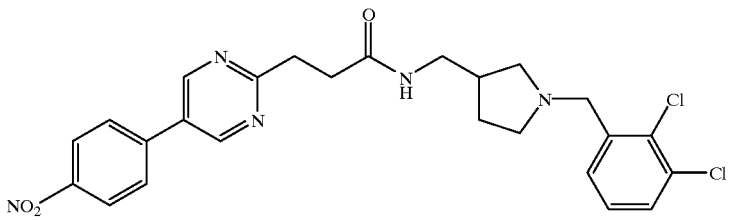

Step 1

Phosphorus oxychloride (83 mL, 0.79 mol) was added slowly to cold, dry dimethyl formamide (100 mL) under $N_2$ at such a rate that the temperature did not rise above 5° C. After addition was complete, 4-nitrophenylacetic acid (48 g, 0.26 mol) was added in one portion and the reaction mixture was heated to 85° C. over 1 h. After 1 h, the reaction mixture was cooled, then poured over ice. Solid sodium perchlorate monohydrate (37 g, 0.26 mol) was added to initiate precipitation of the product as the perchlorate salt. Filtration of the solid, followed by washings with cold water, methanol and ether, gave 2-(4-nitrophenyl)trimethinium perchlorate (81.9 g) as a pale yellow solid.

Step 2

A solution of sodium ethoxide (21% wt/vol, in ethanol, 60 mL, 180 mmol, 3 equiv.) was added in one portion to a suspension of 2-(4-nitrophenyl)trimethinium perchlorate (20.8 g, 60 mmol) and 4-amidinopropionic acid mono hydrochloride salt (9.1 g, 60 mmol) in ethanol (300 mL). The suspension was heated at room temperature overnight. The resulting suspension was filtered, washed with ethanol, cold HCl, water and ether, then dried under high vacuum to give 3-[5-(4-nitrophenyl)pyrimidin-2-yl]-propanoic acid (13.7 g) as a beige solid.

Step 3

1-(3-Dimethylaminopropyl)-3-ethylcarbodiimide hydrochloride (5.8 g, 30 mmol, 1.5 equiv.) was added to a suspension of 3-[4-(4-nitrophenyl)pyrimidin-2-yl]propanoic acid (6.6 g, 24 mmol, 1.2 equiv.), (1-tert-butoxycarbonyl)-3-(RS)-aminomethylpyrrolidine (4.0 g, 20 mmol), 1-hydroxybenzotriazole hydrate (4.1 g, 30 mmol, 1.5 equiv.), and triethylamine (7.0 mL, 50 mmol, 2.5 equiv.) in chloroform (50 mL). Dimethylformamide (100 mL) was added to fully dissolve the reaction components and the solution was stirred at room temperature overnight. The reaction mixture was diluted with ethyl acetate, washed sequentially with 1 M sodium hydroxide, water, 1 M hydrochloric acid, water and brine, then dried sodium sulfate and concentrated to afford a light brown solid. This material was washed with ether to afford clean N-[1-(2,3-dichlorobenzyl)pyrrolidin-3-(RS)-ylmethyl]-3-[5-(4-nitrophenyl)pyrimidin-2-yl]propionamide (4.9 g).

Example 6

Synthesis of N-[1-(2,3-dichlorobenzyl)pyrrolidin-3-(RS)-ylmethyl]-3-[5-(4-aminophenyl)pyrimidin-2-yl]propionamide

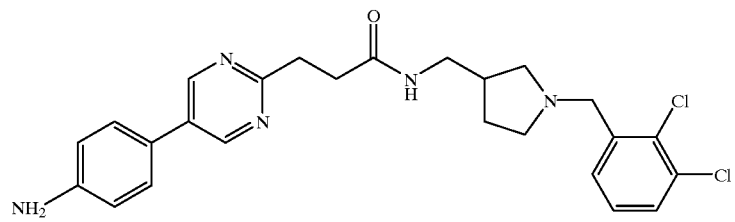

Hydrogen gas (balloon pressure) was introduced into a vessel containing Pd/C (10%, 100 mg, 0.1 mmol, 0.05 equiv.) in a solution of N-[1-(2,3-dichlorobenzyl)-pyrrolidin-3-(RS)-ylmethyl]-3-[5-(4-nitrophenyl)pyrimidin-2-yl]propionamide (1.0 g, 2.2 mmol) in methanol (30 mL). After 1.5 h, the reaction was terminated by purging with $N_2$ and the reaction mixture was filtered through celite® and concentrated. The yellow residue was dissolved in ethyl acetate, then taken into the aqueous phase using 1 M hydrochloric acid. The aqueous phase was basified to pH 11, then extracted thoroughly with ethyl acetate. The organic fractions were combined and washed with brine, then dried sodium sulfate and concentrated to afford N-[1-(2,3-dichlorobenzyl)pyrrolidin-3-(RS)-ylmethyl]-3-[5-(4-aminophenyl)pyrimidin-2-yl]propionamide as a yellow crystalline solid (630 mg).

Example 7

Synthesis of N-(1-(2,3-dichlorobenzyl)pyrrolidin-3-(RS)-ylmethyl)-2-[5-(4-methoxyphenyl)pyrimidin-2-ylsulfanyl]acetamide

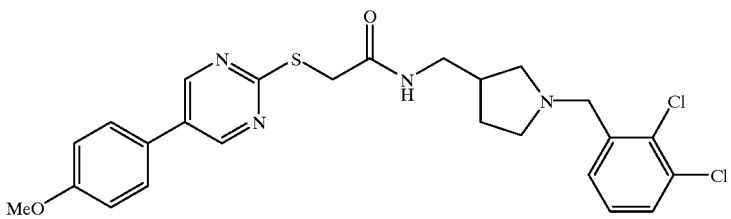

Step 1

Benzaldehyde (5.3 g, 50 mmol) was added to a solution of 3-(RS)-aminomethylpyrrolidine (5.0 g, 50 mmol) in toluene (anhydrous, 100 mL) in a 250 mL flask at room temperature under $N_2$. A Dean-Stark apparatus and condenser were fitted, the reaction vessel well lagged and the reaction mixture heated at a strong reflux for 4 h. The reaction mixture was cooled to room temperature and di-tert-butyl dicarbonate (5.3 g, 50 mmol) was added portionwise and the resulting solution was stirred at room temperature overnight. The reaction mixture was concentrated on the rotavap then the residue was diluted with 1 M NaHSO4 (80 mL, 80 mmol, 1.6 equiv.) and stirred vigorously for 2 h. The reaction mixture was washed with ether to remove unwanted organic byproducts, then basified with 1 M NaOH to pH 7. Further extraction with ethyl acetate removed additional unwanted byproducts. The aqueous solution was then made strongly basic (pH 12) with 1 M NaOH and extracted thoroughly with ethyl acetate. The organic layer was washed with brine, dried with sodium sulfate, then concentrated to give 3-(RS)-aminomethyl-1-tert-butoxycarbonylpyrrolidine as a colorless oil which was used directly without further purification.

Step 2

3-(RS)-aminomethyl-1-tert-butoxycarbonylpyrrolidine (6.0 g, 30 mmol) in methylene chloride (15 mL) was added dropwise to a cold (0° C.) solution of chloroacetylchloride (2.4 mL, 30 mmol) and diisopropylethylamine (5.5 mL, 32 mmol) in methylene chloride under $N_2$. After 1 h, an additional 0.5 equiv. of chloroacetyl chloride and diisopropylamine were added. After being left at 0° C. overnight, the reaction mixture was diluted with ethyl acetate and washed briefly with water and brine, then dried over sodium sulfate and concentrated to give N-(1-tert-butoxycarbonylpyrrolidin- 3-(RS)-ylmethyl)-2-chloroacetamide as a dark brown oil which was used without further purification.

Step 3

A solution of sodium ethoxide (21% wt/vol, 15 mL, 45 mmol, 1.5 equiv.) was added to a suspension of 2-(4-methoxyphenyl)trimethinium perchlorate (10.0 g, 30 mmol) and thiourea (3.0 g, 40 mmol, 1.3 equiv.) in ethanol (200 mL) (see, Krecmerova, M.; Hrebabecky, H.; Masojidkova, M.; Holy, A., Collect. Czech. Chem. Commun., 61, 458, (1996)]. The reaction mixture was heated at 60° C. for 2 h. Additional quantities of thiourea and sodium ethoxide were added to the starting amounts and the reaction mixture was heated at 60° C. for an additional 1 h. The yellow suspension was cooled to room temperature, quenched with acetic acid (10 mL) and filtered. The solid was washed with water and ethanol and dried under high vacuum to give 5-(4-methoxyphenyl)-1H-pyrimidine-2-thione as a free flowing yellow powder (6.0 g).

Step 4

5-(4-Methoxyphenyl)-1H-pyrimidine-2-thione (0.70 g, 3 mmol) was added to a solution of the N-(1-tert-butoxycarbonylpyrrolidin-3-(RS)-ylmethyl)-2-chloroacetamide (1.15 g, ~80% purity, ~3 mmol) and diisopropylethylamine (0.9 mL, 5 mmol, 1.5 equiv.) in dry acetonitrile. An ethanolic solution of sodium ethoxide (2.7 M, 1.2 mL, 3.2 mmol) and dimethylformamide (20 mL) were added in order to dissolve the starting mercaptan. The resulting dark brown solution was stirred at room temperature for 2 h. The reaction mixture was concentrated and the residue was chromatographed on silica gel (50–100% ethyl acetate in hexane). Fractions containing the major product were combined and concentrated to an oily residue. Trituration of the oil with ether afforded pure N-(1-tert-butoxycarbonylpyrrolidin-3-(RS)-ylmethyl)-2-[5-(4-methoxyphenyl)pyrimidin-2-ylthio]-acetamide (0.60 g, 44%) as a pale yellow solid.

Step 5

Neat anhydrous trifluoroacetic acid (3 mL) was added to a solution of N-(1-tert-butoxycarbonylpyrrolidin-3-(RS)-ylmethyl)-2-[5-(4-methoxyphenyl)pyrimidin-2-ylthio]-acetamide (0.60 g, 1.3 mmol) in methylene chloride (20 mL) at room temperature. Gas evolution was apparent immediately upon addition of the acid. After 30 min., the reaction mixture was concentrated using a Teflon dryvac system, and was then further concentrated under high vacuum to give N-(pyrrolidin-3-(RS)-ylmethyl)-2-[5-(4-methoxyphenyl) pyrimidin-2-ylthio]acetamide which was dissolved in 10 mL dichloroethane (0.13 mmol/mL).

Step 6

2,3-Dichlorobenzaldehyde (115 mg, 0.66 mmol, 1.5 equiv.) was added to N-(pyrrolidin-3-(RS)-ylmethyl)-2-[5-(4-methoxyphenyl)pyrimidin-2-ylthio]acetamide in dichloroethane (3.4 mL, 0.44 mmol). Excess Na(OAc)$_3$BH (0.2 g, 0.9 mmol, ~3 equiv.) was added and the resulting suspension was stirred vigorously overnight. The reaction mixture was diluted with ether and quenched with 1 M hydrochloric acid to afford a cloudy mixture. The organic layer was carefully removed and the aqueous phase made basic with 5 M aqueous sodium hydroxide to pH 11. After thorough extraction with ethyl acetate, the combined organic phases was washed with brine, then dried over sodium sulfate and concentrated. Chromatography on silica (0–10% methanol in ethyl acetate) afforded N-(1-(2,3-dichlorobenzyl) pyrrolidin-3-(RS)-ylmethyl)-2-[5-(4-methoxyphenyl) pyrimidin-2-ylsulfanyl]acetamide that was converted to the hydrochloride salt using 4 M hydrochloric acid solution in dioxane and ether (60 mg).

Proceeding as described in Step 6 above, but substituting 2,3-dichloro-benzylaldehyde (115 mg, 0.66 mmol, 1.5 equiv.) with 3,4-dichlorobenzaldehyde gave N-(1-(3,4-dichlorobenzyl)pyrrolidin-3-(RS)-ylmethyl)-2-[5-(4-methoxyphenyl)pyrimidin-2-ylsulfanyl]acetamide hydrochloride salt.

Proceeding as described in Step 6 above, but substituting 2,3-dichloro-benzylaldehyde with 3,4-methylenedioxybenzaldehyde gave N-(1-(3,4-methylenedioxybenzyl)pyrrolidin-3-(RS)-ylmethyl)-2-[5-(4-methoxyphenyl)pyrimidin-2-ylsulfanyl]-acetamide hydrochloride salt.

Example 8

Synthesis of N-[1-(3,4-dichlorobenzyl)pyrrolidin-3-(RS)-ylmethyl]-2-[5-(4-methoxyphenyl)pyrimidin-2-yloxy]acetamide

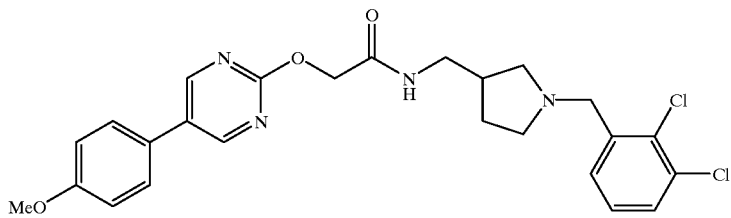

Step 1

The procedure for the synthesis of 5-bromo-2-hydroxypyrimidine used is a variation of that published by Crosby and Berthold, *J. Chem. Soc.* 25, 1916, (1960). To a solution of 2-hydroxypyrimidine hydrochloride (100 g, 0.75 mol) in water (1.2 L) was added bromine (135 g, 0.84 mol) slowly with stirring. The reaction mixture was continuously stirred for about 30 min., until the red color of the solution became lighter. The solution was heated to 80° C. to drive of excess $Br_2$ and HBr. The solvent was concentrated further under vacuum and the residue recrystallized from 90% aqueous ethanol to afford 5-bromo-2-hydroxypyrimidine (111 g).

Step 2

Phosphorus oxychloride (225 mL, 2.4 mol, 1.4 equiv.) was added to a mixture of 5-bromo-2-hydroxypyrimidine (30 g, 0.17 mol) and dimethylaniline (7.5 mL) and the solution was heated at reflux under $N_2$ for 4 h. The dark brown reaction mixture was cooled, poured over ice and extracted with ether. The organic phase was washed with bicarbonate solution, dried sodium sulfate and concentrated to afford 5-bromo-3-chloropyrimidine (25 g, 75%) [see, Goodby, J. W.; Hird, M.; Lewis, R. A.; Toyne, K. J.,*J. Chem. Soc., Chem. Commun.,* 2719, (1996)].

Step 3

The synthesis of (5-bromopyrimidin-2-yloxy)acetic acid followed the protocol described for similar analogues by Coppola, G. M.; Hardtmann, G. E.; Huegi, B. S. *J. Heterocyl. Chem.,* 17, 1479, (1980). Sodium hydride (5.0 g, 60% dispersion in mineral oil, 124 mmol, 1.8 equiv.) was washed twice with dry hexane under $N_2$, then added portionwise to a solution of methyl glycolate (9.4 g, 103 mmol, 1.5 equiv.) in toluene (150 mL). The reaction mixture was stirred at room temperature for 30 min., then 5-bromo-3-chloropyrimidine (13.3 g, 69 mmol) in toluene (50 mL) was added. The reaction mixture was heated at 60° C. overnight and concentrated. The residue was stirred rapidly with 1 M aqueous sodium hydroxide (excess) for 30 min., washed with ether, then acidified to with 4 M hydrochloric acid. The resulting precipitate was collected and washed with cold water. The filtrate was extracted further with ethyl acetate, and the organic phase washed with brine, then dried sodium sulfate and concentrated to give (5-bromopyrimidin-2-yloxy)acetic acid (10.3 g).

Step 4

To a solution of 3-(RS)-aminomethyl-1-tert-butoxycarbonylpyrrolidine in dichloroethane (17 mL) were sequentially added diisopropylethylamine (5.1 mL), a solution of 2-(5-bromopyrimidin-2-yloxy)acetic acid (2.9 g, 12.2 mmol, 1.1 equiv.) in tetrahydrofuran (43 mL), 1-hydroxybenzotriazole hydrate (2.4 g, 17.5 mmol, 1.5 equiv.) and 1-(3-dimethyl-aminopropyl)-3-ethylcarbodiimide hydrochloride (3.4 g, 17.6 mmol, 1.5 equiv.). The solution was stirred under $N_2$ overnight. The reaction mixture was diluted with ethyl acetate, washed with 1 M aqueous sodium hydroxide, 1 M hydrochloric acid, water and brine, then dried over sodium sulfate and concentrated. The residue was subjected to flash chromatography to afford clean N-(1-tert-butoxycarbonylpyrrolidin-3-(RS)-ylmethyl)-2-(5-bromopyrimidin-2-yloxy)acetamide (4.2 g).

Step 5

4-Methoxyphenylboronic acid (1.0 g, 6.8 mmol, 1.05 equiv.) was added to a solution of N-(1-tert-butoxycarbonylpyrrolidin-3-(RS)-ylmethyl)-2-(5-bromopyrimidin-2-yloxy)acetamide (2.7 g, 6.5 mmol) in 1-propanol (30 mL). The suspension was stirred until all ingredients had dissolved (~10 min). The resulting solution was treated with palladium acetate (29 mg, 0.13 mmol, 0.02 equiv.), triphenylphosphine (103 mg, 0.39 mmol, 0.06 equiv.), 2 M aqueous sodium carbonate (3.9 mL, 7.8 mmol, 1.2 equiv.) and deionized water (9 mL). The reaction mixture was heated at reflux under $N_2$ for 1 h. Water (20 mL) was added and the $N_2$ inlet was removed. After stirring at room temperature overnight, the reaction mixture was thoroughly extracted with ethyl acetate. The combined organic phase was washed with saturated sodium bicarbonate solution and brine. The organic phase was stirred with activated charcoal for 15 min, dried over sodium sulfate and concentrated. Recrystallization of the residue from ethyl acetate in hexane afforded clean N-(1-tert-butoxycarbonylpyrrolidin-3-(RS)-ylmethyl)-2-(5-(4-methoxyphenyl)pyrimidin-2-yloxy)acetamide (2.1 g). The solid was dissolved into methylene chloride (30 mL) and neat trifluoroacetic acid (5 mL)

added dropwise. After about 1 h, the solution was concentrated to an oil on a Teflon dryvac, then under high vacuum to give N-(pyrrolidin-3-(RS)-ylmethyl)-2-[5-(4-methoxyphenyl)pyrimidin-2-yloxy]acetamide.

Step 6

A stock solution containing N-(pyrrolidin-3-(RS)-ylmethyl)-2-(5-(4-methoxyphenyl)pyrimidin-2-yloxy) acetamide (0.44 mmol) in dichloroethane (10 mL) was added to a solution of 3,4-dichlorobenzaldehyde (85 mg, 0.48 mmol, 1.1 equiv.) and diisopropylethylamine (0.35 mL, 2.0 mmol, 4.5 equiv.) in dichloroethane (5 mL). Excess Na(OAc)₃BH (140 mg, 0.66 mmol, 1.5 equiv.) was added and the reaction mixture was stirred rapidly at room temperature overnight. The reaction mixture was quenched with methanol, concentrated and diluted with 1:1 methanol/dimethyl sulfoxide. The solution was then purified directly using preparative reverse phase chromatography to give, after treatment with 4 M hydrochloric acid in dioxane (1 mL) and concentration, N-[1-(3,4-dichlorobenzyl)pyrrolidin-3-(RS)-ylmethyl]-2-[5-(4-methoxyphenyl)pyrimidin-2-yloxy]-acetamide HCl salt (96 mg).

Example 9

Synthesis of N-[1-(2,3-dichlorobenzyl)pyrrolidin-3-(RS)-ylmethyl]-2-[5-(4-methoxyphenyl)pyrimidin-2-ylamino]acetamide Hydrochloride Salt

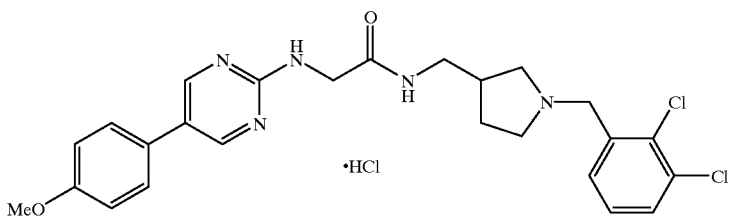

Step 1

An ethanolic solution of sodium ethoxide (2.7 M, 3.8 mL, 10 mmol, 2.9 equiv.) was added to a suspension of 2-(4-methoxyphenyl)trimethinium perchlorate salt (1.1 g, 3.4 mmol) and guanidineacetic acid (0.48 g, 4.0 mmol, 1.2 equiv.) in dehydrated ethanol (20 mL). The reaction mixture was stirred at room temperature for 30 min., then at reflux temperature for 3 h. After cooling, the sodium salt was filtered, and the cake dissolved in 20 mL of water then acidified with 1 M hydrochloric acid. The aqueous layer was extracted with ethyl acetate and the combined organic phases was washed with brine, and dried over sodium sulfate. Removal of the solvent under vacuum afforded a solid which contained ~1:1 mixture of regioisomers. The two components were separated using reversed-phase chromatography to give 2-[5-(4-methoxyphenyl)pyrimidin-2-ylamino]-acetic acid (150 mg) and the regioisomer (100 mg).

Step 2

Solid 1-(3-dimethylaminopropyl)-3-ethylcarbodiimide hydrochloride (14 mg, 0.08 mmol, 1.5 equiv.) was added to a solution of 3-(RS)-aminomethyl-1-(2,3-dichlorobenzyl)-pyrrolidine (13 mg, 0.05 mmol), 2-[5-(3-methoxyphenyl) pyrimidin-2-ylamino]acetic acid (16 mg, 0.06 mmol, 1.2 equiv.), 1-hydroxybenzotriazole hydrate (10 mg, 0.08 mmol, 1.5 equiv.) and diisopropylethylamine (22 mL, 0.13 mmol, 2.5 equiv.) in dimethyl formamide (0.5 mL). The reaction mixture was shaken at room temperature overnight. The reaction mixture was quenched with methanol (0.3 mL), then purified directly by reverse phase preparative HPLC to give N-[1-(2,3-dichlorobenzyl)pyrrolidin-3-(RS)-ylmethyl]-2-[5-(4-methoxyphenyl)pyrimidin-2-ylamino]acetamide HCl salt (11 mg).

Example 10

Synthesis of N-[1-(3,4-dichlorobenzyl)pyrrolidin-3-(RS)-ylmethyl]-4-(2,5-dimethylphenyl)-4-oxo-butyramide Trifluoroacetate Salt

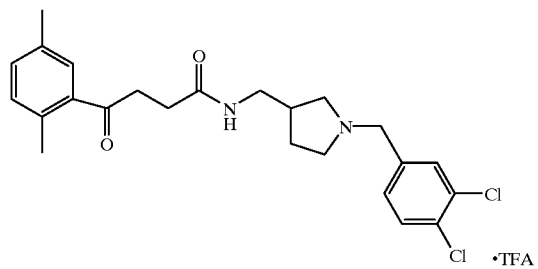

To a solution (1 mL) of 1-(3-dimethylaminopropyl)-3-ethylcarbodiimide hydrochloride (55 mg, 0.28 mmol, 1.8 equiv.), 1-hydroxybenzotriazole hydrate (38 mg, 0.28 mmol, 1.8 equiv.) and triethylamine (43 mL, 0.31 mmol, 2.0 equiv.) in chloroform were added solid 4-(2,5-dimethylphenyl)-4-oxobutyric acid (39 mg, 0.19 mmol, 1.2 equiv.) and 3-(RS)-aminomethyl-1-(3,4-dichlorobenzyl)pyrrolidine (40 mg, 0.16 mmol) in chloroform (1 mL). The reaction mixture was shaken overnight, then concentrated and diluted with dimethylsulfoxide/methanol (1:1, 1 mL). The reaction mixture was purified by reversed phase chromatography to give N-[1-(3,4-dichlorobenzyl)pyrrolidin- 3-(RS)-ylmethyl]-4-(2,5-dimethylphenyl)-4-oxo-butyramide trifluoroacetate salt as a colorless oil (33 mg).

Other Examples

Proceeding as described above but substituting 4-(2,5-dimethylphenyl)-4-oxo-butyric acid with (4-acetylphenoxy) acetic acid gave 2-(4-acetylphenoxy)-N-[1-(3,4-dichlorobenzyl)pyrrolidin-3-(RS)-ylmethyl]acetamide.

Proceeding as described above but substituting 4-(2,5-dimethylphenyl)-4-oxo-butyric acid with N-phenylsulfonylglycine gave 2-benzenesulfonylamino-N-[1-(3,4-dichlorobenzyl)pyrrolidin-3-(RS)-ylmethyl] acetamide.

Proceeding as described above but substituting 4-(2,5-dimethylphenyl)-4-oxobutyric acid with 2-(6-methoxynaphth-2-yl)-2-methylacetic acid gave N-[1-(3,4-dichlorobenzyl)pyrrolidin-3-(RS)-ylmethyl]-2-(6-methoxynaphth-2-yl)propionamide.

Proceeding as described above but substituting 4-(2,5-dimethylphenyl)-4-oxobutyric acid with 3-benzenesulfonylpropionic acid gave 3-benzenesulfonyl-N-[1-(3,4-dichlorobenzyl)pyrrolidin-3-(RS)-ylmethyl]propionamide.

Proceeding as described above but substituting 4-(2,5-dimethylphenyl)-4-oxobutyric acid with (4-thiophen-2-ylpyrazol-1-yl)acetic acid gave N-[1-(3,4-dichloro-benzyl)pyrrolidin-3-(RS)-ylmethyl]-2-(4-thiophen-2-ylpyrazol-1-yl)acetamide.

Proceeding as described above but substituting 4-(2,5-dimethylphenyl)-4-oxobutyric acid with 2-(chloro-3-methylbenzo[b]thiophen-2-yl)acetic acid gave N-[1-(3,4-dichlorobenzyl)pyrrolidin-3-(RS)-ylmethyl]-2-(chloro-3-methylbenzo[b]thiophen-2-yl)acetamide.

Proceeding as described above but substituting 4-(2,5-dimethylphenyl)-4-oxobutyric acid with 2-(4-benzyloxyphenoxy)acetic acid gave 2-(4-benzyloxyphenoxy)-N-[1-(3,4-dichlorobenzyl)pyrrolidin-3-(RS)-ylmethyl]acetamide.

Proceeding as described above but substituting 4-(2,5-dimethylphenyl)-4-oxobutyric acid with 2-methyl-2-(4-thiophenoylphenyl)acetic acid gave N-[1-(3,4-dichlorobenzyl)pyrrolidin-3-(RS)-ylmethyl]-2-(4-thiophenoylphenyl)propionamide.

Proceeding as described above but substituting 4-(2,5-dimethylphenyl)-4-oxobutyric acid with 2-(1-acetylnaphth-2-yloxy)-2-methylacetic acid gave 2-(1-acetyl-naphth-2-yloxy)-N-[1-(3,4-dichlorobenzyl)pyrrolidin-3-(RS)-ylmethyl]propionamide.

Proceeding as described above but substituting 4-(2,5-dimethylphenyl)-4-oxobutyric acid with N-benzoylglycine gave 2-benzoylamino-N-[1-(3,4-dichloro-benzyl)pyrrolidin-3-(RS)-ylmethyl]acetamide.

Proceeding as described above but substituting 4-(2,5-dimethylphenyl)-4-oxobutyric acid with 2-(5,6-dimethylbenzimidazol-1-yl)acetic acid gave N-[1-(3,4-dichlorobenzyl)pyrrolidin-3-(RS)-ylmethyl]-2-(5,6-dimethylbenzimidazol-1-yl)acetamide.

Proceeding as described above but substituting 4-(2,5-dimethylphenyl)-4-oxobutyric acid with 2-(5-methyl-2-phenyloxazol-3-yl)acetic acid gave N-[1-(3,4-dichlorobenzyl)pyrrolidin-3-(RS)-ylmethyl]-2-(5-methyl-2-phenyloxazol-3-yl)acetamide.

Proceeding as described above but substituting 4-(2,5-dimethylphenyl)-4-oxobutyric acid with 2-(3-methyl-2-N-phenylpyrazol-4-yl)acetic acid gave N-[1-(3,4-dichlorobenzyl)pyrrolidin-3-(RS)-ylmethyl]-2-(3-methyl-2-N-phenylpyrazol-4-yl)acetamide.

Proceeding as described above but substituting 4-(2,5-dimethylphenyl)-4-oxobutyric acid with 2-(2-pyrazin-2-ylthiazol-4-yl)acetic acid gave N-[1-(3,4-dichlorobenzyl)pyrrolidin-3-(RS)-ylmethyl]- 2-(2-pyrazin-2-ylthiazol-4-yl)acetamide.

Proceeding as described above but substituting 4-(2,5-dimethylphenyl)-4-oxobutyric acid with 2-(4-methyl-[1,2,3]thiadiazol-5-ylsulfanyl)acetic acid gave N-[1-(3,4-dichlorobenzyl)pyrrolidin-3-(RS)-ylmethyl]-2-(4-methyl-[1,2,3]thiadiazol-5-ylsulfanyl)acetamide.

Proceeding as described above but substituting 4-(2,5-dimethylphenyl)-4-oxobutyric acid with 2-(naphth-2-ylsulfanyl)acetic acid gave N-[1-(3,4-dichlorobenzyl)pyrrolidin-3-(RS)-ylmethyl]-2-(naphth-2-ylsulfanyl)acetamide.

Proceeding as described above but substituting 4-(2,5-dimethylphenyl)-4-oxo-butyric acid with 2-(quinoxalin-2-ylsulfanyl)acetic acid gave N-[1-(3,4-dichloro-benzyl)pyrrolidin-3-(RS)-ylmethyl]-2-(quinoxalin-2-ylsulfanyl)acetamide.

Proceeding as described above but substituting 4-(2,5-dimethylphenyl)-4-oxo-butyric acid with 2-(2-chloro-4-fluorophenylsulfanyl)acetic acid gave 2-(2-chloro-4-fluorophenylsulfanyl)-N-[1-(3,4-dichlorobenzyl)pyrrolidin-3-(RS)-ylmethyl]acetamide.

Proceeding as described above but substituting 4-(2,5-dimethylphenyl)-4-oxobutyric acid with 2-[2-(pyridin-2-yl)-6-trifluoromethylpyrimidin-4-ylsulfanyl]acetic acid gave N-[1-(3,4-dichlorobenzyl)pyrrolidin-3-(RS)-ylmethyl]-2-[2-(pyridin-2-yl)-6-trifluoromethylpyrimidin-4-ylsulfanyl]acetamide.

Proceeding as described above but substituting 4-(2,5-dimethylphenyl)-4-oxobutyric acid with 2-[5-(4-chlorophenyl)pyrimidin-4-ylsulfanyl]acetic acid gave 2-[5-(4-chlorophenyl)pyrimidin-4yl-sulfanyl]-N-[1-(3,4-dichlorobenzyl)pyrrolidin-3-(RS)-ylmethyl]acetamide.

Proceeding as described above but substituting 4-(2,5-dimethylphenyl)-4-oxobutyric acid with 2-(3,4-methylenedioxyphenyl)acetic acid and 3-aminomethyl-1-(3,4-dichlorobenzyl)pyrrolidine with 3-aminomethyl-1-(3,4-methylenedioxybenzyl)pyrrolidine gave N-[1-(3,4-methylenedioxybenzyl)pyrrolidin-3-(RS)-ylmethyl]-2-(3,4-methylenedioxyphenyl)acetamide.

Proceeding as described above but substituting 4-(2,5-dimethylphenyl)-4-oxobutyric acid with 2-(3-phenylpyrazol-1-yl)acetic acid and 3-aminomethyl-1-(3,4-dichlorobenzyl)pyrrolidine with 3-aminomethyl-1-benzylpyrrolidine gave N-[1-(benzyl)-pyrrolidin-3-(RS)-ylmethyl]-2-(3-phenylpyrazol-1-yl)acetamide.

Proceeding as described above but substituting 4-(2,5-dimethylphenyl)-4-oxobutyric acid with 2-(3-fluoro-4-hydroxyphenyl)acetic acid and 3-aminomethyl-1-(3,4-dichlorobenzyl)pyrrolidine with 3-(S)-aminomethyl-1-(2,3-dichlorobenzyl)pyrrolidine gave N-[1-(2,3-dichlorobenzyl)pyrrolidin-3-(S)-ylmethyl]-2-(3-fluoro-4-hydroxyphenyl)-acetamide.

Proceeding as described above but substituting 4-(2,5-dimethylphenyl)-4-oxobutyric acid with 2-(3-acetylaminophenyl)acetic acid and 3-aminomethyl-1-(3,4-dichlorobenzyl)pyrrolidine with 3-(S)-aminomethyl-1-(2,3-dichlorobenzyl)pyrrolidine gave N-[1-(2,3-dichlorobenzyl)pyrrolidin-3-(S)-ylmethyl]-2-(3-acetylaminophenyl)-acetamide.

Example 11

Synthesis of 1-[1-(3,4-methylenedioxybenzyl)pyrrolidin-3-(RS)-ylmethyl]-3-m-tolylurea TFA Salt

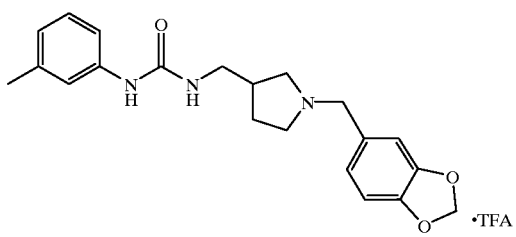

Neat 3-methylphenylisocyanate (16 mg, 0.12 mmol, 1.1 equiv.) was added to a solution of 3-(RS)-aminomethyl-1-(3,4-methylenedioxybenzyl)pyrrolidine (28 mg, 0.12 mmol)

in tetrahydrofuran (1 mL) at room temperature. The reaction mixture was shaken overnight, concentrated to dryness and diluted with dimethyl sulfoxide/methanol (1:1, 1 mL). The solution was purified using reversed phase chromatography to give, after evaporation of the solvents, 1-[1-(3,4-methylenedioxybenzyl)pyrrolidin-3-(RS)-ylmethyl]-3-m-tolylurea as the TFA salt (26 mg).

Other Examples

Proceeding as described above but substituting 3-methylphenylisocyanate with 4-methoxyphenylisocyanate gave 1-[1-(3,4-methylenedioxybenzyl)pyrrolidin-3-(RS)-ylmethyl]-3-(4-methoxyphenyl)urea.

Proceeding as described above but substituting 3-methylphenylisocyanate with phenethylisocyanate gave 1-[1-(3,4-methylenedioxybenzyl)pyrrolidin-3-(RS)-ylmethyl]-3-(2-phenylethyl)urea.

Proceeding as described above but 3-aminomethyl-1-(3,4-methylenedioxybenzyl)pyrrolidine with 3-(RS)-aminomethyl-1-(3-phenylbenzyl)pyrrolidine gave 1-[1-(3-phenylbenzyl)pyrrolidin-3-(RS)-ylmethyl]-3-m-tolylurea.

Proceeding as described above but substituting 3-(RS)-aminomethyl-1-(3,4-methylenedioxybenzyl)pyrrolidine with 3-aminomethyl-1-(3,4-dichlorobenzyl)-pyrrolidine and 3-methylphenylisocyanate with 1-(naphth-1-yl)ethylisocyanate gave 1-[1-(3,4-dichlorobenzyl)pyrrolidin-3-(RS)-ylmethyl]-3-[1-(naphth-1-yl)ethyl]urea.

Example 12

Synthesis of N-[1-(3,4-dichlorobenzyl)pyrrolidin-3-(RS)-ylmethyl]-2-(9H-1,3,4,9-tetraazafluoren-2-ylsulfanyl)acetamide

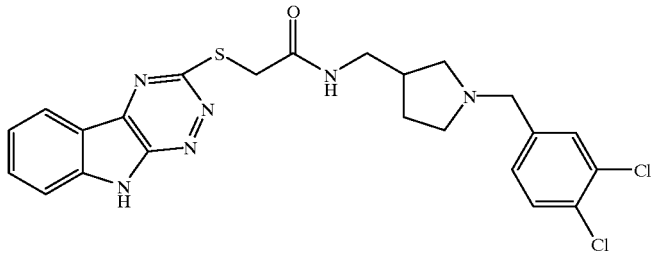

Solid (9H-1,3,4,9-tetraazafluoren-2-ylsulfanyl)acetic acid (390 mg, 1.5 mmol, 1.2 equiv.) was added to a solution of 1-(3-dimethylaminopropyl)-3-ethylcarbodiimide hydrochloride (360 mg, 1.9 mmol, 1.5 equiv.), 1-hydroxybenzotriazole hydrate (260 mg, 1.9 mmol, 1.5 equiv.) and triethylamine (0.65 mL, 4.6 mmol, 3.7 equiv.) in chloroform (10 mL). 3-(RS)-Aminomethyl-1-(3,4-dichlorobenzyl)pyrrolidine (320 mg, 1.2 mmol) was added and the suspension was made homogeneous upon addition of dimethylformamide (5 mL). The brown solution was stirred for 14 h, then concentrated in vacuo. The residue was diluted with ethyl acetate and washed with 1 M sodium hydroxide. The organic phase was concentrated to dryness and the residue purified by chromatography (5→10% methanol in CHCl$_3$) to provide N-[1-(3,4-dichlorobenzyl)-pyrrolidin-3-(RS)-ylmethyl]-2-(9H-1,3,4,9-tetraazafluoren-2-ylsulfanyl)acetamide as a pale yellow solid. The solid was dissolved into 4 M HCl in dioxane (1 mL) and the mixture concentrated under vacuum to afford pure product as its hydrochloride salt (250 mg).

Example 13

Formulation Examples

The following are representative pharmaceutical formulations containing a compound of Formula (I).

| Tablet formulation The following ingredients are mixed intimately and pressed into single scored tablets. | |
|---|---|
| Ingredient | Quantity per tablet, mg |
| compound of this invention | 400 |
| cornstarch | 50 |
| croscarmellose sodium | 25 |
| lactose | 120 |
| magnesium stearate | 5 |

| Capsule formulation The following ingredients are mixed intimately and loaded into a hard-shell gelatin capsule. | |
|---|---|
| Ingredient | Quantity per capsule, mg |
| compound of this invention | 200 |
| lactose, spray-dried | 148 |
| magnesium stearate | 2 |

| Suspension formulation The following ingredients are mixed to form a suspension for oral administration. | |
|---|---|
| Ingredient | Amount |
| compound of this invention | 1.0 g |
| fumaric acid | 0.5 g |

| -continued | |
|---|---|
| sodium chloride | 2.0 g |
| methyl paraben | 0.15 g |
| propyl paraben | 0.05 g |
| granulated sugar | 25.5 g |
| sorbit (70% solution) | 12.85 g |
| Veegum K (Vanderbilt Co.) | 1.0 g |
| flavoring | 0.035 ml |
| colorings | 0.5 mg |
| distilled water | q.s. to 100 ml |

| Injectable formulation The following ingredients are mixed to form an injectable formulation. | |
|---|---|
| Ingredient | Amount |
| compound of this invention | 0.2 g |
| sodium acetate buffer solution, 0.4M | 2.0 ml |

-continued

| | |
|---|---|
| HCl (1N) or NaOH (1N) | q.s. to suitable pH |
| water (distilled, sterile) | q.s. to 20 ml |

Liposomal formulation
The following ingredients are mixed to form a liposomal formulation.

| Ingredient | Amount |
|---|---|
| compound of this invention | 10 mg |
| L-α-phosphatidylcholine | 150 mg |
| tert-butanol | 4 ml |

Freeze dry the sample and lyopholize overnight. Reconstitute the sample with 1 ml 0.9% saline solution. Liposome size can be reduced by sonication Example 14

CCR-3 Receptor Binding Assay—In Vitro

The CCR-3 antagonistic activity of the compounds of the invention was determined by their ability to inhibit the binding of $^{125}I$ eotaxin to CCR-3 L1.2 transfectant cells ((see Ponath, P. D. et al., *J. Exp. Med.*, Vol. 183, 2437–2448, (1996)).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin (BSA), 0.02% sodium azide, pH 7.24) such that the final DMSO concentration was 2%. 25 µl of the test solution or only buffer with DMSO (control samples) was added to each well, followed by the addition of 25 µl of $^{125}I$-eotaxin (100 pmol) (NEX314, New England Nuclear, Boston, Mass.) and $1.5 \times 10^5$ of the CCR-3 L1.2 transfected cells in 25 µl binding buffer. The final reaction volume was 75 µl.

After incubating the reaction mixture for 1 h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 min. 25 µl/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}I$-eotaxin binding to the CCR-3 L 1.2 transfected cells by 50%) for compounds in Tables I–V of the invention was between 0.02 and 200 µM.

Example 15

Inhibition of Eotaxin Mediated Chemotaxis of CCR-3 L1.2 Transfectant Cells—In Vitro Assay The CCR-3 antagonistic activity of the compounds of this invention was determined by measuring the inhibition of eotaxin mediated chemotaxis of the CCR-3 L1.2 transfectant cells, using a slight modification of the method described in Ponath, P. D. et al., *J. Clin. Invest.* 97: 604–612 (1996). The assay was performed in a 24-well chemotaxis plate (Costar Corp., Cambridge, Mass.). CCR-3 L1.2 transfectant cells were grown in culture medium containing RPMI 1640, 10% Hyclone™ fetal calf serum, 55 mM 2-mercaptoethanol and Geneticin 418 (0.8 mg/ml). 18–24 hours before the assay, the transfected cells were treated with n-butyric acid at a final concentration of 5 mM/$1 \times 10^6$ cells/ml, isolated and resuspended at $1 \times 10^7$ cells/ml in assay medium containing equal parts of RPMI 1640 and Medium 199 (M 199) with 0.5% bovine serum albumin.

Human eotaxin suspended in phosphate buffered saline at 1 mg/ml was added to bottom chamber in a final concentration of 100 nm. Transwell culture inserts (Costar Corp., Cambridge, Mass.) having 3 micron pore size were inserted into each well and L1.2 cells ($1 \times 10^6$) were added to the top chamber in a final volume of 100 µl. Test compounds in DMSO were added both to the top and bottom chambers such that the final DMSO volume was 0.5%. The assay was performed against two sets of controls. The positive control contained cells with no test compound in the top chamber and only eotaxin in the lower chamber. The negative control contained cells with no test compound in the top chamber and neither eotaxin nor test compound in lower chamber. The plate was incubated at 37° C. After 4 h, the inserts were removed from the chambers and the cells that had migrated to the bottom chamber were counted by pipetting out 500 µl of the cell suspension from the lower chamber to 1.2 ml Cluster tubes (Costar) and counting them on a FACS for 30 sec.

The $IC_{50}$ value (concentration of test compound required to reduce eotaxin mediated chemotaxis of CCR-3 L 1.2 transfected cells by 50%) for representative compounds of the invention was between 0.006 to 1.1 µm.

Example 16

Inhibition of Eotaxin Mediated Chemotaxis of Human Eosinophils—In Vitro Assay

The ability of compounds of the invention to inhibit eotaxin mediated chemotaxis of human eosinophils was assessed using a slight modification of procedure described in Carr, M. W. et al., *Proc. Natl. Acad. Sci. USA*, 91: 3652–3656 (1994). Experiments were performed using 24 well chemotaxis plates (Costar Corp., Cambridge, Mass.). Eosinophils were isolated from blood using the procedure described in PCT Application, Publication No. WO 96/22371. The endothelial cells used were the endothelial cell line ECV 304 obtained from European Collection of Animal Cell Cultures (Porton Down, Salisbury, U.K.). Endothelial cells were cultured on 6.5 mm diameter Biocoat® Transwell tissue culture inserts (Costar Corp., Cambridge, Mass.) with a 3.0 µM pore size. Culture media for ECV 304 cells consisted of M199, 10% Fetal Calf Serum, L-glutamine and antibiotics. Assay media consisted of equal parts RPMI 1640 and M199, with 0.5% BSA. 24 h before the assay $2 \times 10^5$ ECV 304 cells were plated on each insert of the 24-well chemotaxis plate and incubated at 37° C. 20 nM of eotaxin diluted in assay medium was added to the bottom chamber. The final volume in bottom chamber was 600 µl. The endothelial coated tissue culture inserts were inserted into each well. $10^6$ eosinophil cells suspended in 100 µl assay buffer were added to the top chamber. Test compounds dissolved in DMSO were added to both top and bottom chambers such that the final DMSO volume in each well was 0.5%. The assay was performed against two sets of controls. The positive control contained cells in the top chamber and eotaxin in the lower chamber. The negative control contained cells in the top chamber and only assay buffer in the lower chamber. The plates were incubated at 37° C. in 5% $CO_2$/95% air for 1–1.5 h.

The cells that had migrated to the bottom chamber were counted using flow cytometry. 500 µl of the cell suspension from the lower chamber was placed in a tube, and relative cell counts were obtained by acquiring events for a set time period of 30 seconds.

Compounds of this invention were active in this assay.

Example 17

Inhibition of Eosinophil Influx Into the Lungs of Ovalbumin Sensitized Balb/c Mice by CCR-3 Antagonist—In Vivo Assay The ability of the compounds of the invention to inhibit leukocyte infiltration into the lungs was determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25g were sensitized with OA (10 μg in 0.2 ml aluminum hydroxide solution) intraperitoneally on days 1 and 14. After a week, the mice were divided into ten groups. Test compound or only vehicle (control group) or anti-eotaxin antibody (positive control group) was administered either intraperitoneally, subcutaneously or orally. After 1 h, the mice were placed in a Plexiglass box and exposed to OA aerosol generated by a PARISTAR™ nebulizer (PARI, Richmond, Va.) for 20 min. Mice which had not been sensitized or challenged were included as negative control. After 24 or 72 h, the mice were anesthetized (urethane, approx. 1 g/kg, i.p.), a tracheal cannula (PE 60 tubing) was inserted and the lungs were lavaged four times with 0.3 ml PBS. The BAL fluid was transferred into plastic tubes and kept on ice. Total leukocytes in a 20 μl aliquot of the BAL fluid was determined by Coulter Counter™ (Coulter, Miami, Fla.). Differential leukocyte counts were made on Cytospin™ preparations which had been stained with a modified Wright's stain (DiffQuick™) by light microscopy using standard morphological criteria.

Compounds of this invention were active in this assay. The $ID_{50}$ for the compounds of this invention in this assay is between 30 and 50 mgs/kg.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound selected from compounds of Formula (I):

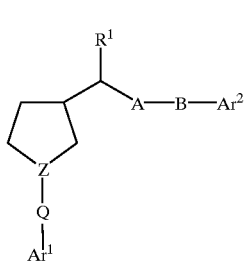

(I)

Z is —N— or —(N⁺R)—X⁻ wherein R is alkyl, haloalkyl, aralkyl, hydroxyalkyl, carboxyalkyl, alkoxycarbonylalkyl, or cyanoalkyl, and X⁻ is a pharmaceutically acceptable counterion;

$Ar^1$ and $Ar^2$ are, independently of each other, aryl or heteroaryl;

Q is a straight or branched alkylene chain of 1–3 carbon atoms;

$R^1$ is hydrogen or alkyl;

A is either:

(I) —N($R^2$)C(O)— when:

B is:
(i) an alkylene chain of 1–4 carbon atoms inclusive wherein one of the carbon atoms may optionally be replaced by a group selected from —C(O)—, —N($R^4$)—, —O—, —S(O)$_n$— (where n is 0, 1 or 2), —N$R^5$C(O)— and —N($R^6$)SO$_2$—; or
(ii) an alkynylene chain;

wherein:
$R^2$ is hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; and $R^4$, $R^5$ and $R^6$ are, independently of each other, hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; or (II) a group selected from —N($R^2$)C(S)—, —N($R^2$)C(O)N($R^3$)—, —N($R^2$)C(S)N($R^3$)—, —N($R^2$)SO$_2$—, —N($R^2$)SO$_2$N($R^3$)—, —N($R^2$)C(O)O—, and —OC(O)N($R^3$)— when:

B is:
(i) a bond;
(ii) an alkylene chain of 1–4 carbon atoms inclusive wherein one of the carbon atoms may optionally be replaced by a group selected from —C(O)—, —N($R^4$)—, —O—, —S(O)$_n$— (where n is 0, 1 or 2), —N$R^5$C(O)— and —N($R^6$)SO$_2$—;
(iii) an alkenylene chain; or
(iv) an alkynylene chain;

wherein:
$R^3$ is hydrogen, alkyl, acyl, haloalkyl, heteroalkyl, heterocyclylalkyl, or -(alkylene)—C(O)—Z' where Z' is alkyl, haloalkyl, alkoxy, haloalkyloxy, hydroxy, amino, or mono- or disubstituted amino; and $R^2$, $R^4$, $R^5$ and $R^6$ are as defined above; and prodrugs, individual isomers, mixtures of isomers and pharmaceutically acceptable salts thereof.

2. The compound of claim 1 wherein Z is —N—; $R^1$ is hydrogen and A is —NHC(O)—.

3. The compound of claim 2 wherein $Ar^1$ is a naphthyl or a phenyl ring substituted with one, two, or three substituents selected from alkyl, cyano, nitro, halo, methylenedioxy, ethylenedioxy, alkoxy or phenoxy.

4. The compound of claim 3 wherein Q and B are —CH$_2$—.

5. The compound of claim 4 wherein $Ar^2$ is an aryl ring.

6. The compound of claim 5 wherein:
$Ar^1$ is a phenyl ring substituted with one, two, or three substituents selected from methyl, chloro, fluoro, bromo, or methylenedioxy; and
$Ar^2$ is a phenyl ring optionally substituted with one, two, or three substituents selected from alkoxy, alkylthio, halo, amino, —NHC(O)R' (where R' is alkyl or optionally substituted phenyl), hydroxy, or —SO$_2$Me.

7. The compound of claim 6 wherein $Ar^1$ is 3-chlorophenyl, 4-chlorophenyl, 3,4-difluorophenyl, 3-chloro-4-fluorophenyl, 4-chloro-3-fluorophenyl, 4-fluoro-3-methoxyphenyl, 2,4-difluorophenyl, 3,4-ethylenedioxyphenyl, 2,3-dichlorophenyl, 3,4-dichlorophenyl, or 3,4-methylenedioxyphenyl.

8. The compound of claim 7 wherein $Ar^2$ is a phenyl ring optionally substituted with one, two, or three substituents selected from methyl, methylthio, hydroxy, methoxy, acetyl, chloro, fluoro, bromo, or —NHC(O)R' (where R' is methyl or a phenyl ring optionally substituted with one, two, three, or four substituents selected from methyl, methoxy, fluoro, or chloro).

9. The compound of claim 8 wherein $Ar^2$ is phenyl, 3-(2,5-difluoro-4-chlorophenylcarbonylamino)phenyl, 4-(2,3,4,5-tetrafluorophenylcarbonylamino)phenyl, 3-(2,4-dimethoxyphenylcarbonylamino)phenyl, 3-(phenylcarbonylamino)phenyl, 3-acetylaminophenyl, 3-fluoro-4-hydroxyphenyl, 3-fluorophenyl, 3-methoxyphenyl, or 4-hydroxy-3-methoxyphenyl.

10. The compound of claim 9 wherein:
$Ar^1$ is 2,3-dichlorophenyl; and
$Ar^2$ is 3-fluoro-4-hydroxyphenyl;
namely, N-[1-(2,3-dichlorobenzyl)pyrrolidin-3-(S)-ylmethyl]-2-(3-fluoro-4-hydroxyphenyl)acetamide.

11. The compound of claim 9 wherein:
$Ar^1$ is 2,3-dichlorophenyl; and
$Ar^2$ is 3-acetylaminophenyl;
namely, N-[1-(2,3-dichlorobenzyl)pyrrolidin-3-(S)-ylmethyl]-2-(3-acetylaminophenyl)acetamide.

12. The compound of claim 3 wherein:
Q is —CH$_2$— and B is —(CH$_2$)$_2$—.

13. The compound of claim 12 wherein $Ar^2$ is a heteroaryl ring.

14. The compound of claim 13 wherein:
$Ar^1$ is a phenyl ring substituted with one, two, or three substituents methyl, chloro, fluoro, bromo, or methylenedioxy.

15. The compound of claim 14 wherein $Ar^1$ is 3-chlorophenyl, 4-chlorophenyl, 3,4-difluorophenyl, 3-chloro-4-fluorophenyl, 4-chloro-3-fluorophenyl, 4-fluoro-3-methoxyphenyl, 2,4-difluorophenyl, 3,4-ethylenedioxyphenyl, 2,3-dichlorophenyl, 3,4-dichlorophenyl, or 3,4-methylenedioxyphenyl.

16. The compound of claim 15 wherein $Ar^2$ is a pyrimidin-2-yl ring optionally substituted at the 5-position with a phenyl ring which is optionally substituted with one, two, or three substituents selected from methyl, methoxy, methylthio, chloro, fluoro, vinyl, or dimethylamino.

17. The compound of claim 16 wherein $Ar^2$ is pyrimidin-2-yl, 5-phenylpyrimidin-2-yl, 5-(4-methoxyphenyl)pyrimidin-2-yl, 5-(3,4-dimethoxyphenyl)pyrimidin-2-yl, 5-(4-methylthiophenyl)pyrimidin-2-yl, 5-(4-dimethylaminophenyl)pyrimidin-2-yl, 5-(4-methylphenyl)pyrimidin-2-yl or 5-(4-fluorophenyl)pyrimidin-2-yl.

18. The compound of claim 17 wherein:
$Ar^1$ is 2,3-dichlorophenyl; and
$Ar^2$ is 5-(4-methoxyphenyl)pyrimidin-2-yl;
namely, N-[1-(2,3-dichlorobenzyl)pyrrolidin-3-ylmethyl]-3-[5-(4-methoxyphenyl)pyrimidin-2-yl]propionamide.

19. The compound of claim 17 wherein:
$Ar^1$ is 3,4-dichlorophenyl; and
$Ar^2$ is 5-(4-methoxyphenyl)pyrimidin-2-yl;
namely, N-[1-(3,4-dichlorobenzyl)pyrrolidin-3-ylmethyl]-3-[5-(4-methoxyphenyl)pyrimidin-2-yl]propionamide.

20. The compound of claim 3 wherein Q is —CH$_2$— and B is —CH$_2$S—.

21. The compound of claim 20 wherein:
$Ar^2$ is a heteroaryl ring.

22. The compound of claim 21 wherein:
$Ar^1$ is a phenyl ring optionally substituted with one, two, or three substituents methyl, chloro, fluoro, bromo, or methylenedioxy.

23. The compound of claim 22 wherein $Ar^1$ is 3-chlorophenyl, 4-chlorophenyl, 3,4-difluorophenyl, 3-chloro-4-fluorophenyl, 4-chloro-3-fluorophenyl, 4-fluoro-3-methoxyphenyl, 2,4-difluorophenyl, 3,4-ethylenedioxyphenyl, 2,3-dichlorophenyl, 3,4-dichlorophenyl, or 3,4-methylenedioxyphenyl.

24. The compound of claim 23 wherein $Ar^2$ is a pyrimidin-2-yl ring optionally substituted at the 5-position with a phenyl ring which optionally substituted with one, two, or three substituents selected from methyl, methoxy, methylthio, chloro, fluoro, vinyl or dimethylamino.

25. The compound of claim 24 wherein $Ar^2$ is pyrimidin-2-yl, 5-phenylpyrimidin-2-yl, 5-(4-methoxyphenyl)pyrimidin-2-yl, 5-(3,4-dimethoxyphenyl)pyrimidin-2-yl, 5-(4-methylthiophenyl)pyrimidin-2-yl, 5-(4-dimethylaminophenyl)pyrimidin-2-yl, 5-(4-methylphenyl)pyrimidin-2-yl or 5-(4-fluorophenyl)pyrimidin-2-yl.

26. The compound of claim 25 wherein:
$Ar^1$ is 2,3-dichlorophenyl; and
$Ar^2$ is 5-(4-methoxyphenyl)pyrimidin-2-yl;
namely, N-[1-(2,3-dichlorobenzyl)pyrrolidin-3-ylmethyl]-2-[5-(4-methoxyphenyl)pyrimidin-2-ylsulfanyl]acetamide.

27. The compound of claim 26 wherein:
$Ar^1$ is 3,4-dichlorophenyl; and
$Ar^2$ is 5-(4-methoxyphenyl)pyrimidin-2-yl;
namely, N-[1-(3,4-dichlorobenzyl)pyrrolidin-3-ylmethyl]-2-[5-(4-methoxyphenyl)pyrimidin-2-ylsulfanyl]acetamide.

28. The compound of claim 26 wherein:
$Ar^1$ is 3,4-methylenedioxyphenyl; and
$Ar^2$ is 5-(4-methoxyphenyl)pyrimidin-2-yl;
namely, N-[1-(3,4-methylenedioxybenzyl)pyrrolidin-3-ylmethyl]-2-[5-(4-methoxyphenyl)pyrimidin-2-ylsulfanyl]acetamide.

29. The compound of claim 3 wherein Q is —CH$_2$— and B is —CH$_2$O—.

30. The compound of claim 29 wherein:
$Ar^2$ is a heteroaryl ring.

31. The compound of claim 30 wherein:
Ar¹ is a phenyl ring optionally substituted with one, two, or three substituents methyl, chloro, fluoro, bromo, or methylenedioxy.

32. The compound of claim 31 wherein Ar¹ is 3-chlorophenyl, 4-chlorophenyl, 3,4-difluorophenyl, 3-chloro-4-fluorophenyl, 4-chloro-3-fluorophenyl, 4-fluoro-3-methoxyphenyl, 2,4-difluorophenyl, 3,4-ethylenedioxyphenyl, 2,3-dichlorophenyl, 3,4-dichlorophenyl, or 3,4-methylenedioxyphenyl.

33. The compound of claim 32 wherein Ar² is a pyrimidin-2-yl ring optionally substituted at the 5-position with a phenyl ring which optionally substituted with one, two, or three substituents selected from methyl, methoxy, methylthio, chloro, fluoro, vinyl or dimethylamino.

34. The compound of claim 33 wherein Ar² is pyrimidin-2-yl, 5-phenylpyrimidin-2-yl, 5-(4-methoxyphenyl)pyrimidin-2-yl, 5-(3,4-dimethoxyphenyl)pyrimidin-2-yl, 5-(4-methylthiophenyl)pyrimidin-2-yl, 5-(4-dimethylaminophenyl)pyrimidin-2-yl, 5-(4-methylphenyl)pyrimidin-2-yl or 5-(4-fluorophenyl)pyrimidin-2-yl.

35. The compound of claim 34 wherein:
Ar¹ is 2,3-dichlorophenyl; and
Ar² is 5-(4-methoxyphenyl)pyrimidin-2-yl;
namely, N-[1-(2,3-dichlorobenzyl)pyrrolidin-3-ylmethyl]-2-[5-(4-methoxyphenyl)pyrimidin-2-yloxy]acetamide.

36. The compound of claim 34 wherein:
Ar¹ is 3,4-dichlorophenyl; and
Ar² is 5-(3,4-dimethoxyphenyl)pyrimidin-2-yl;
namely, N-[1-(3,4-dichlorobenzyl)pyrrolidin-3-ylmethyl]-2-[5-(3,4-dimethoxyphenyl)pyrimidin-2-yloxy]acetamide.

37. The compound of claim 34 wherein:
Ar¹ is 2,3-dichlorophenyl; and
Ar² is 5-(4-methylthiophenyl)pyrimidin-2-yl;
namely, N-[1-(2,3-dichlorobenzyl)pyrrolidin-3-ylmethyl]-2-[5-(4-methylthiophenyl)pyrimidin-2-yloxy]acetamide.

38. The compound of claim 1 wherein R¹ is hydrogen and A is —NHC(O)NH—.

39. The compound of claim 38 wherein Ar¹ is a naphthyl or a phenyl ring optionally substituted with one, two or three substituents selected from alkyl, cyano, nitro, halo, methylenedioxy, ethylenedioxy, alkoxy or phenoxy.

40. The compound of claim 39 wherein Q is —CH₂— and B is a bond or —CH₂—.

41. The compound of claim 40 wherein Ar² is an aryl ring.

42. The compound of claim 41 wherein:
Ar¹ is a phenyl ring optionally substituted with one, two, or three substituents selected from methyl, chloro, fluoro, bromo, or methylenedioxy; and
Ar² is a phenyl ring optionally substituted with one or two substituents selected from alkyl or alkoxy.

43. The compound of claim 42 wherein Ar¹ is 3-chlorophenyl, 4-chlorophenyl, 3,4-difluorophenyl, 3-chloro-4-fluorophenyl, 4-chloro-3-fluorophenyl, 4-fluoro-3-methoxyphenyl, 2,4-difluorophenyl, 3,4-ethylenedioxyphenyl, 2,3-dichlorophenyl, 3,4-dichlorophenyl, or 3,4-methylenedioxyphenyl.

44. The compound of claim 43 wherein Ar² is a phenyl ring optionally substituted with one or two substituents selected from methyl or methoxy.

45. The compound of claim 44 wherein Ar² is phenyl, 3-methylphenyl, 4-methylphenyl, 3-methoxyphenyl or 4-methoxyphenyl.

46. A process for preparing a compound of claim 1, which comprises reacting a compound of Formula (IIa) where R¹, Q, and Ar¹ are as defined in claim 1:

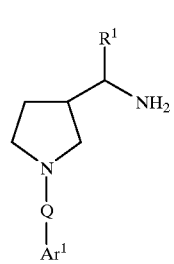

(IIa)

(i) with an acylating agent of formula Ar²—B—COL where L is a leaving group under acylating reaction conditions or an acid anhydride of formula (Ar²—B—CO)₂O to provide a compound of Formula (I) where A is —N(R²)CO— wherein R² is hydrogen; or (ii) with an amine of formula Ar²—B—NH(R³) where R³ is as defined in the Summary of the Invention, in the presence of a suitable coupling agent or an isocyanate of formula Ar²—B—N=C=O or a carbamoyl halide of formula Ar²—B—N(R³)—C(O)L where R³ is as defined in the Summary of the Invention and L is a halo group to provide a compound of Formula (I) where A is —N(R²)CON(R³)— wherein R² is hydrogen; or (iii) with an amine of formula Ar²—B—NH(R³) where R³ is as defined in the Summary of the Invention, in the presence of a suitable coupling agent or an isothiocyanate of formula Ar²—B—N=C=S or a thiocarbamoyl halide of formula Ar²—B—N(R³)—C(S)L where R³ is as defined in the Summary of the Invention and L is a halo group to provide a compound of Formula (I) where A is —N(R²)C(S)N(R³)— wherein R² is hydrogen; or (iv) with a sulfonylating agent of formula Ar²—B—SO₂L or Ar²—B—N(R³)-SO₂L where R³ is as defined in the Summary of the Invention and L is a leaving group under sulfonylating reaction conditions to provide a compound of Formula (I) where A is —N(R²)SO₂— or —N(R²)SO₂N(R³)— wherein R² is hydrogen; or (v) with an alcohol of formula Ar²—B—OH in the presence of a suitable coupling agent to provide a compound of Formula (I) where A is —N(R²)C(O)O— wherein R² is hydrogen; and (vi) optionally converting a compound of Formula (I) prepared in Steps (i) to (v) above, where R² is hydrogen to a compound of Formula (I) where R² is not hydrogen; and (vii) optionally reacting a compound of Formula (I) prepared in Steps (i) to (vi) above, with an alkylating agent of formula RX where R is alkyl and X is a leaving group under alkylating conditions to provide a corresponding compound of Formula (I) where Z is —(N⁺R)—X⁻; and (viii) optionally replacing one counterion in the compound of Formula (I) prepared in Step (vii) above, with another counterion; and (ix) optionally converting the compound of Formula (I) prepared in Steps (i) to (viii) above, to the corresponding acid addition salt by treatment with an acid.

47. A process for preparing a compound of claim 1, which comprises:

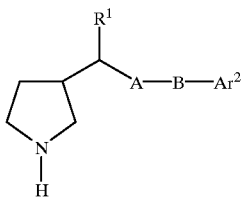
(IIb)

(i) reacting a compound of formula (IIb) where $R^1$, A, B and $Ar^2$ are as defined above, with an alkylating agent of formula $Ar^1$—Q—Y where $Ar^1$ is as defined in claim 1 and Y is a leaving group under alkylating reaction conditions to provide a compound of Formula (I); and (ii) optionally reacting a compound of Formula (I) prepared in Step (i) above, with an alkylating agent of formula RX where R is alkyl and X is a leaving group under alkylating conditions to provide a corresponding compound of Formula (I) where Z is —($N^+R$)—$X^-$; and (iii) optionally replacing one counterion in the compound of Formula (I) prepared in Step (ii) above, with another counterion; and (iv) optionally converting the compound of Formula (I) prepared in Steps (i) to (iii) above, to the corresponding acid addition salt by treatment with an acid.

48. A pharmaceutical composition comprising a therapeutically effective amount of a compound of claim 1 and a pharmaceutically acceptable excipient.

49. A method of treatment of a disease in a mammal treatable by administration of a CCR-3 antagonist, comprising administration to the mammal of a therapeutically effective amount of a compound of claim 1.

50. The method of claim 49, wherein the disease is asthma.

* * * * *